(12) United States Patent
Hubelbank et al.

(10) Patent No.: US 11,051,875 B2
(45) Date of Patent: Jul. 6, 2021

(54) MULTIPURPOSE ELECTROSURGICAL DEVICE

(71) Applicant: Medtronic Advanced Energy LLC, Minneapolis, MN (US)

(72) Inventors: David Hubelbank, Litchfield, NH (US); Roger D. Greeley, Portsmouth, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 783 days.

(21) Appl. No.: 15/216,370

(22) Filed: Jul. 21, 2016

(65) Prior Publication Data

US 2017/0056099 A1 Mar. 2, 2017

Related U.S. Application Data

(60) Provisional application No. 62/208,931, filed on Aug. 24, 2015.

(51) Int. Cl.
| | |
|---|---|
| *A61B 18/14* | (2006.01) |
| *A61B 18/12* | (2006.01) |
| *A61B 18/00* | (2006.01) |
| *A61B 17/00* | (2006.01) |

(52) U.S. Cl.
CPC ........ *A61B 18/1477* (2013.01); *A61B 18/148* (2013.01); *A61B 2017/00473* (2013.01); *A61B 2018/0063* (2013.01); *A61B 2018/00577* (2013.01); *A61B 2018/00589* (2013.01); *A61B 2018/00601* (2013.01); *A61B 2018/00958* (2013.01); *A61B 2018/126* (2013.01); *A61B 2018/1253* (2013.01); *A61B 2018/1467* (2013.01); *A61B 2018/1475* (2013.01); *A61B 2018/1495* (2013.01)

(58) Field of Classification Search
CPC ...... A61B 18/14–16; A61B 2018/0091; A61B 2018/00916; A61B 2018/00958; A61B 2018/1467; A61B 2018/1475; A61B 2018/1495
See application file for complete search history.

(56) References Cited

U.S. PATENT DOCUMENTS

| | | |
|---|---|---|
| 2,888,928 A | 6/1959 | Seige |
| 3,682,130 A | 8/1972 | Jeffers |
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |

(Continued)

FOREIGN PATENT DOCUMENTS

| | | |
|---|---|---|
| WO | WO96/04955 A2 | 2/1996 |
| WO | WO2007-037785 | 4/2007 |

(Continued)

*Primary Examiner* — Ronald Hupczey, Jr.
(74) *Attorney, Agent, or Firm* — Dicke, Billig & Czaja, PLLC

(57) ABSTRACT

A multipurpose electrosurgical device is configurable in a bipolar mode and a monopolar mode using a three-conductor electrical input. The device includes a switching mechanism that provides signals corresponding with a first function and a second function in a monopolar mode. The switching mechanism also provides a signal corresponding with a third function in a bipolar mode.

20 Claims, 16 Drawing Sheets

(56) References Cited

U.S. PATENT DOCUMENTS

| | | | |
|---|---|---|---|
| 4,244,371 A | 1/1981 | Farin | |
| 4,248,224 A | 2/1981 | Jones | |
| 4,275,734 A | 6/1981 | Mitchiner | |
| 4,276,874 A | 7/1981 | Wolvek et al. | |
| 4,278,090 A | 7/1981 | van Gerven | |
| 4,321,931 A | 3/1982 | Hon | |
| 4,342,218 A | 8/1982 | Fox | |
| 4,355,642 A | 10/1982 | Alferness | |
| 4,377,168 A | 3/1983 | Rzasa et al. | |
| 4,381,007 A | 4/1983 | Doss | |
| 4,519,389 A | 5/1985 | Gudkin et al. | |
| 4,598,698 A | 7/1986 | Siegmund | |
| 4,601,290 A | 7/1986 | Effron et al. | |
| 4,657,016 A | 4/1987 | Garito et al. | |
| 4,664,110 A | 5/1987 | Schanzlin | |
| 4,671,274 A | 6/1987 | Sorochenko | |
| 4,736,749 A | 4/1988 | Lundback | |
| 4,779,611 A | 10/1988 | Grooters et al. | |
| 4,802,475 A | 2/1989 | Weshahy | |
| 4,827,927 A * | 5/1989 | Newton | A61B 18/12 606/37 |
| 4,919,129 A | 4/1990 | Weber et al. | |
| 4,931,047 A | 6/1990 | Broadwin et al. | |
| 4,932,952 A | 6/1990 | Wojciechowicz, Jr. | |
| 4,943,290 A | 7/1990 | Rexroth et al. | |
| 4,950,232 A | 8/1990 | Ruzicka et al. | |
| 4,985,030 A | 1/1991 | Melzer et al. | |
| 4,998,933 A | 3/1991 | Eggers et al. | |
| 5,190,541 A | 3/1993 | Abele et al. | |
| 5,195,959 A | 3/1993 | Smith | |
| 5,234,428 A | 8/1993 | Kaufman | |
| 5,254,117 A | 10/1993 | Rigby et al. | |
| 5,281,215 A | 1/1994 | Milder | |
| 5,309,896 A | 5/1994 | Moll et al. | |
| 5,316,000 A | 5/1994 | Chapelon et al. | |
| 5,317,878 A | 6/1994 | Bradshaw et al. | |
| 5,318,525 A | 6/1994 | West et al. | |
| 5,322,520 A | 6/1994 | Milder | |
| 5,323,781 A | 6/1994 | Ideker et al. | |
| 5,324,255 A | 6/1994 | Passafaro et al. | |
| 5,324,284 A | 6/1994 | Imran | |
| 5,324,286 A | 6/1994 | Fowler | |
| 5,330,521 A | 7/1994 | Cohen | |
| 5,334,181 A | 8/1994 | Rubinsky et al. | |
| 5,334,193 A | 8/1994 | Nardella | |
| 5,336,220 A | 8/1994 | Ryan et al. | |
| 5,348,554 A | 9/1994 | Imran et al. | |
| 5,353,783 A | 10/1994 | Nakao et al. | |
| 5,354,258 A | 10/1994 | Dory | |
| 5,361,752 A | 11/1994 | Moll et al. | |
| 5,383,874 A | 1/1995 | Jackson et al. | |
| 5,385,148 A | 1/1995 | Lesh et al. | |
| 5,395,312 A | 3/1995 | Desai | |
| 5,396,887 A | 3/1995 | Imran | |
| 5,397,304 A | 3/1995 | Truckai | |
| 5,400,770 A | 3/1995 | Nakao et al. | |
| 5,400,783 A | 3/1995 | Pomeranz et al. | |
| 5,401,272 A | 3/1995 | Perkins | |
| 5,403,309 A | 4/1995 | Coleman et al. | |
| 5,403,311 A | 4/1995 | Abele et al. | |
| 5,405,376 A | 4/1995 | Mulier et al. | |
| 5,409,483 A | 4/1995 | Campbell et al. | |
| 5,417,709 A | 5/1995 | Slater | |
| 5,423,807 A | 6/1995 | Milder | |
| 5,423,811 A | 6/1995 | Imran et al. | |
| 5,427,119 A | 6/1995 | Swartz et al. | |
| 5,431,168 A | 7/1995 | Webster, Jr. | |
| 5,431,649 A | 7/1995 | Mulier et al. | |
| 5,433,708 A | 7/1995 | Nichols et al. | |
| 5,435,308 A | 7/1995 | Gallup et al. | |
| 5,437,651 A | 8/1995 | Todd et al. | |
| 5,441,503 A | 8/1995 | Considine et al. | |
| 5,443,463 A | 8/1995 | Stern et al. | |
| 5,443,470 A | 8/1995 | Stern et al. | |
| 5,445,638 A | 8/1995 | Rydell et al. | |
| 5,450,843 A | 9/1995 | Moll et al. | |
| 5,452,582 A | 9/1995 | Longsworth | |
| 5,452,733 A | 9/1995 | Sterman et al. | |
| 5,460,629 A | 10/1995 | Shlain et al. | |
| 5,462,545 A | 10/1995 | Wang et al. | |
| 5,465,717 A | 11/1995 | Imran et al. | |
| 5,469,853 A | 11/1995 | Law et al. | |
| 5,472,876 A | 12/1995 | Fahy | |
| 5,478,309 A | 12/1995 | Sweezer et al. | |
| 5,478,330 A | 12/1995 | Imran et al. | |
| 5,486,193 A | 1/1996 | Bourne et al. | |
| 5,487,385 A | 1/1996 | Avitall | |
| 5,487,757 A | 1/1996 | Truckai et al. | |
| 5,490,819 A | 2/1996 | Nicholas et al. | |
| 5,496,271 A | 3/1996 | Burton et al. | |
| 5,496,312 A | 3/1996 | Klicek | |
| 5,497,774 A | 3/1996 | Swartz et al. | |
| 5,498,248 A | 3/1996 | Milder | |
| 5,500,012 A | 3/1996 | Brucker et al. | |
| 5,505,700 A | 4/1996 | Leone | |
| 5,505,730 A | 4/1996 | Edwards | |
| 5,516,505 A | 5/1996 | McDow | |
| 5,520,682 A | 5/1996 | Baust et al. | |
| 5,522,870 A | 6/1996 | Ben-Zion | |
| 5,536,267 A | 7/1996 | Edwards et al. | |
| 5,540,562 A | 7/1996 | Giter | |
| 5,542,196 A | 8/1996 | Hirsch et al. | |
| 5,542,945 A | 8/1996 | Fritzsch | |
| 5,545,195 A | 8/1996 | Lennox et al. | |
| 5,545,200 A | 8/1996 | West et al. | |
| 5,549,661 A | 8/1996 | Kordis et al. | |
| 5,555,883 A | 9/1996 | Avitall | |
| 5,556,397 A | 9/1996 | Long et al. | |
| 5,558,671 A | 9/1996 | Yates | |
| 5,560,362 A | 10/1996 | Silwa, Jr. et al. | |
| 5,562,503 A * | 10/1996 | Ellman | A61B 18/14 200/51.03 |
| 5,562,702 A | 10/1996 | Huitema et al. | |
| 5,562,720 A | 10/1996 | Stern et al. | |
| 5,569,241 A | 10/1996 | Edwards | |
| 5,569,243 A | 10/1996 | Kortenbach et al. | |
| 5,571,088 A | 11/1996 | Lennox et al. | |
| 5,571,215 A | 11/1996 | Sterman et al. | |
| 5,573,424 A | 11/1996 | Poppe | |
| 5,575,766 A | 11/1996 | Swartz et al. | |
| 5,575,788 A | 11/1996 | Baker et al. | |
| 5,575,810 A | 11/1996 | Swanson et al. | |
| 5,578,007 A | 11/1996 | Imran | |
| 5,582,609 A | 12/1996 | Swanson et al. | |
| 5,588,432 A | 12/1996 | Crowley | |
| 5,590,657 A | 1/1997 | Cain et al. | |
| 5,595,183 A | 1/1997 | Swanson et al. | |
| 5,599,346 A | 2/1997 | Edwards et al. | |
| 5,605,539 A | 2/1997 | Buelna et al. | |
| 5,607,462 A | 3/1997 | Imran | |
| 5,617,854 A | 4/1997 | Munsif | |
| 5,630,837 A | 5/1997 | Crowley | |
| 5,643,197 A | 7/1997 | Brucker et al. | |
| 5,647,869 A | 7/1997 | Goble et al. | |
| 5,656,029 A | 8/1997 | Imran et al. | |
| 5,658,278 A | 8/1997 | Imran et al. | |
| 5,637,090 A | 9/1997 | McGee et al. | |
| 5,671,747 A | 9/1997 | Connor | |
| 5,673,695 A | 10/1997 | McGee et al. | |
| 5,676,662 A | 10/1997 | Fleischhacker et al. | |
| 5,676,692 A | 10/1997 | Sanghvi et al. | |
| 5,676,693 A | 10/1997 | Lafontaine | |
| 5,678,550 A | 10/1997 | Bassen et al. | |
| 5,680,860 A | 10/1997 | Imran | |
| 5,681,278 A | 10/1997 | Igo et al. | |
| 5,681,294 A | 10/1997 | Osborne et al. | |
| 5,681,308 A | 10/1997 | Edwards et al. | |
| 5,687,723 A | 11/1997 | Avitall | |
| 5,687,737 A | 11/1997 | Branham et al. | |
| 5,688,267 A | 11/1997 | Panescu et al. | |
| 5,690,611 A | 11/1997 | Swartz et al. | |
| 5,697,536 A | 12/1997 | Eggers et al. | |
| 5,697,882 A | 12/1997 | Eggers et al. | |
| 5,697,925 A | 12/1997 | Taylor | |

(56) References Cited

U.S. PATENT DOCUMENTS

| | | | |
|---|---|---|---|
| 5,697,927 A | 12/1997 | Imran et al. | |
| 5,697,928 A | 12/1997 | Walcott et al. | |
| 5,713,942 A | 2/1998 | Stern | |
| 5,716,389 A | 2/1998 | Walinsky et al. | |
| 5,718,241 A | 2/1998 | Ben-Haim et al. | |
| 5,718,701 A | 2/1998 | Shai et al. | |
| 5,720,775 A | 2/1998 | Lanard | |
| 5,722,402 A | 3/1998 | Swanson et al. | |
| 5,730,074 A | 3/1998 | Peter | |
| 5,730,127 A | 3/1998 | Avitall | |
| 5,730,704 A | 3/1998 | Avitall | |
| 5,733,280 A | 3/1998 | Avitall | |
| 5,735,280 A | 4/1998 | Sherman et al. | |
| 5,743,903 A | 4/1998 | Stern et al. | |
| 5,755,760 A | 5/1998 | Maguire et al. | |
| 5,766,167 A | 6/1998 | Eggers et al. | |
| 5,769,846 A | 6/1998 | Edwards et al. | |
| 5,782,828 A | 7/1998 | Chen et al. | |
| 5,785,706 A | 7/1998 | Bednarek | |
| 5,788,636 A | 8/1998 | Curley | |
| 5,792,140 A | 8/1998 | Tu et al. | |
| 5,797,905 A | 8/1998 | Fleischman et al. | |
| 5,797,960 A | 8/1998 | Stevens et al. | |
| 5,735,290 A | 9/1998 | Nelson et al. | |
| 5,800,428 A | 9/1998 | Nelson et al. | |
| 5,800,482 A | 9/1998 | Pomeranz et al. | |
| 5,810,764 A | 9/1998 | Eggers et al. | |
| 5,810,802 A | 9/1998 | Panescu et al. | |
| 5,827,216 A | 10/1998 | Igo et al. | |
| 5,836,947 A | 11/1998 | Fleischman et al. | |
| 5,840,030 A | 11/1998 | Ferek-Petric et al. | |
| 5,843,021 A | 12/1998 | Edwards et al. | |
| 5,843,152 A | 12/1998 | Tu et al. | |
| 5,844,349 A | 12/1998 | Oakley et al. | |
| 5,846,187 A | 12/1998 | Wells et al. | |
| 5,846,191 A | 12/1998 | Wells et al. | |
| 5,849,028 A | 12/1998 | Chen | |
| 5,861,021 A | 1/1999 | Thome et al. | |
| 5,871,523 A | 2/1999 | Fleischman et al. | |
| 5,871,525 A | 2/1999 | Edwards et al. | |
| 5,873,845 A | 2/1999 | Cline et al. | |
| 5,873,855 A | 2/1999 | Eggers et al. | |
| 5,876,399 A | 3/1999 | Chia et al. | |
| 5,879,295 A | 3/1999 | Li et al. | |
| 5,879,296 A | 3/1999 | Ockuly et al. | |
| 5,879,348 A | 3/1999 | Owens et al. | |
| 5,881,732 A | 3/1999 | Sung et al. | |
| 5,882,346 A | 3/1999 | Pomeranz et al. | |
| 5,885,278 A | 3/1999 | Fleischman | |
| 5,891,142 A | 4/1999 | Eggers et al. | |
| 5,893,848 A | 4/1999 | Negus et al. | |
| 5,895,355 A | 4/1999 | Schaer | |
| 5,895,417 A | 4/1999 | Pomeranz et al. | |
| 5,897,553 A | 4/1999 | Mulier | |
| 5,897,554 A | 4/1999 | Chia et al. | |
| 5,899,898 A | 5/1999 | Arless et al. | |
| 5,899,899 A | 5/1999 | Arless et al. | |
| 5,902,289 A | 5/1999 | Swartz et al. | |
| 5,904,711 A | 5/1999 | Flom et al. | |
| 5,906,580 A | 5/1999 | Kline-Schoder et al. | |
| 5,906,587 A | 5/1999 | Zimmon | |
| 5,906,606 A | 5/1999 | Chee et al. | |
| 5,908,029 A | 6/1999 | Knudson et al. | |
| 5,913,854 A | 6/1999 | Maguire et al. | |
| 5,916,213 A | 6/1999 | Haissaguerre et al. | |
| 5,916,214 A | 6/1999 | Cosio et al. | |
| 5,921,924 A | 7/1999 | Avitall | |
| 5,921,982 A | 7/1999 | Lesh et al. | |
| 5,925,045 A | 7/1999 | Reimels et al. | |
| 5,927,284 A | 7/1999 | Borst et al. | |
| 5,931,810 A | 8/1999 | Grabek | |
| 5,931,848 A | 8/1999 | Saadat | |
| 5,935,123 A | 8/1999 | Edwards et al. | |
| 5,944,715 A | 8/1999 | Goble et al. | |
| 5,928,191 A | 9/1999 | Houser et al. | |
| 5,954,661 A | 9/1999 | Greenspon et al. | |
| 5,971,980 A | 10/1999 | Sherman | |
| 5,971,983 A | 10/1999 | Lesh | |
| 5,975,919 A | 11/1999 | Arnett et al. | |
| 5,980,516 A | 11/1999 | Mulier et al. | |
| 5,989,248 A | 11/1999 | Tu et al. | |
| 5,993,412 A | 11/1999 | Deily et al. | |
| 5,993,447 A | 11/1999 | Blewett et al. | |
| 6,004,316 A | 12/1999 | Laufer | |
| 6,004,319 A | 12/1999 | Goble et al. | |
| 6,007,499 A | 12/1999 | Martin et al. | |
| 6,010,500 A | 1/2000 | Sherman et al. | |
| 6,012,457 A | 1/2000 | Lesh | |
| 6,015,391 A | 1/2000 | Rishton et al. | |
| 6,016,811 A | 1/2000 | Knopp et al. | |
| 6,018,676 A | 1/2000 | Davis et al. | |
| 6,019,757 A | 2/2000 | Scheldrup | |
| 6,024,733 A | 2/2000 | Eggers et al. | |
| 6,030,381 A | 2/2000 | Jones et al. | |
| 6,036,687 A | 3/2000 | Laufer et al. | |
| 6,042,556 A | 3/2000 | Beach et al. | |
| 6,048,333 A | 4/2000 | Lennox et al. | |
| 6,056,744 A | 5/2000 | Edwards | |
| 6,056,745 A | 5/2000 | Panescu et al. | |
| 6,056,746 A | 5/2000 | Goble | |
| 6,056,747 A | 5/2000 | Saadat et al. | |
| 6,063,081 A | 5/2000 | Mulier | |
| 6,066,139 A | 5/2000 | Ryan et al. | |
| 6,068,653 A | 5/2000 | LaFontaine | |
| 6,071,279 A | 6/2000 | Whayne et al. | |
| 6,083,237 A | 7/2000 | Huitema et al. | |
| 6,086,585 A | 7/2000 | Hovda et al. | |
| 6,088,894 A | 7/2000 | Oakley | |
| 6,096,037 A | 8/2000 | Mulier | |
| 6,113,592 A | 9/2000 | Taylor | |
| 6,113,596 A * | 9/2000 | Hooven | A61B 18/14 606/42 |
| 6,117,101 A | 9/2000 | Diederich et al. | |
| 6,120,496 A | 9/2000 | Whayne et al. | |
| 6,141,576 A | 10/2000 | Littmann et al. | |
| 6,142,993 A | 11/2000 | Whayne et al. | |
| 6,142,994 A | 11/2000 | Swanson et al. | |
| 6,149,620 A | 11/2000 | Baker et al. | |
| 6,152,920 A | 11/2000 | Thompson et al. | |
| 6,161,543 A | 12/2000 | Cox et al. | |
| 6,165,174 A | 12/2000 | Jacobs et al. | |
| 6,190,384 B1 | 2/2001 | Ouchi | |
| 6,193,716 B1 | 2/2001 | Shannon, Jr. | |
| 6,210,406 B1 | 4/2001 | Webster | |
| 6,210,410 B1 | 4/2001 | Farin et al. | |
| 6,210,411 B1 | 4/2001 | Hofmann et al. | |
| 6,212,426 B1 | 4/2001 | Swanson | |
| 6,216,704 B1 | 4/2001 | Ingle et al. | |
| 6,217,528 B1 | 4/2001 | Koblish et al. | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,231,591 B1 | 5/2001 | Desai | |
| 6,235,020 B1 | 5/2001 | Cheng et al. | |
| 6,235,024 B1 | 5/2001 | Tu | |
| 6,237,605 B1 | 5/2001 | Vaska et al. | |
| 6,238,347 B1 | 5/2001 | Nix et al. | |
| 6,238,387 B1 | 5/2001 | Miller, III | |
| 6,238,393 B1 | 5/2001 | Mulier | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,251,092 B1 | 6/2001 | Qin et al. | |
| 6,251,110 B1 | 6/2001 | Wampler | |
| 6,251,128 B1 | 6/2001 | Knopp et al. | |
| 6,258,087 B1 | 7/2001 | Edwards et al. | |
| 6,264,650 B1 | 7/2001 | Hovda et al. | |
| 6,266,551 B1 | 7/2001 | Osadchy et al. | |
| 6,270,471 B1 | 8/2001 | Hechel et al. | |
| 6,283,988 B1 | 9/2001 | Laufer et al. | |
| 6,283,989 B1 | 9/2001 | Laufer et al. | |
| 6,293,943 B1 | 9/2001 | Panescu et al. | |
| 6,296,619 B1 | 10/2001 | Brisken et al. | |
| 6,299,633 B1 | 10/2001 | Laufer | |

(56) References Cited

U.S. PATENT DOCUMENTS

| | | |
|---|---|---|
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | Bloom et al. |
| RE4,794 E | 6/2003 | Eggers et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,652,514 B2 * | 11/2003 | Ellman .............. A61B 18/12 606/37 |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | Bloom et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 7,066,586 B2 | 6/2006 | da Silva |
| 7,156,845 B2 | 1/2007 | Mulier et al. |
| 7,166,106 B2 | 1/2007 | Bartel et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | Bloom et al. |
| 7,608,072 B2 | 10/2009 | Swanson |
| 7,645,277 B2 | 1/2010 | Bloom et al. |
| 7,651,494 B2 | 1/2010 | Bloom et al. |
| 7,691,050 B2 | 4/2010 | Gellman |
| 7,736,361 B2 | 6/2010 | Palanker |
| 7,811,282 B2 | 10/2010 | McClurken |
| 7,815,634 B2 | 10/2010 | Bloom et al. |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | McClurken et al. |
| 8,105,323 B2 | 1/2012 | Buysse et al. |
| 8,172,828 B2 | 4/2012 | Chang et al. |
| 8,177,783 B2 | 5/2012 | Davison et al. |
| 8,216,233 B2 | 7/2012 | McClurken |
| 8,323,276 B2 | 12/2012 | Palanker et al. |
| 8,348,946 B2 | 1/2013 | McClurken |
| 8,361,068 B2 | 1/2013 | McClurken |
| 8,388,642 B2 | 3/2013 | Muni et al. |
| 8,414,572 B2 | 4/2013 | Davison et al. |
| 8,475,455 B2 | 7/2013 | McClurken |
| 2002/0049483 A1 | 4/2002 | Knowlton |
| 2002/0062131 A1 | 5/2002 | Gallo, Sr. |
| 2002/0082643 A1 | 6/2002 | Kammerer et al. |
| 2003/0014050 A1 | 1/2003 | Sharkey et al. |

(56) References Cited

U.S. PATENT DOCUMENTS

| | | |
|---|---|---|
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Shankey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0171525 A1 | 8/2005 | Rioux |
| 2005/0209564 A1 | 9/2005 | Bonner |
| 2005/0267454 A1 | 12/2005 | Hissong |
| 2005/0273097 A1 | 12/2005 | Ryan |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0111709 A1 | 5/2006 | Goble et al. |
| 2007/0049920 A1 | 3/2007 | Bloom et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0103494 A1 | 5/2008 | Rioux |
| 2008/0207208 A1 | 8/2008 | Schutz |
| 2008/0262489 A1 | 10/2008 | Steinke |
| 2009/0264879 A1 | 10/2009 | Bloom et al. |
| 2009/0306655 A1 | 12/2009 | Stangenes |
| 2010/0069904 A1 | 3/2010 | Cunningham |
| 2010/0100095 A1 | 4/2010 | Bloom et al. |
| 2010/0160906 A1 | 6/2010 | Jarrard |
| 2010/0168743 A1 | 7/2010 | Stone et al. |
| 2010/0204560 A1 | 8/2010 | Salahieh et al. |
| 2010/0241178 A1 | 9/2010 | Tilson et al. |
| 2011/0028965 A1 | 2/2011 | McClurken |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0095461 A1 | 4/2012 | Herscher et al. |
| 2012/0101496 A1 | 4/2012 | McClurken et al. |
| 2012/0116397 A1 | 5/2012 | Rencher et al. |
| 2012/0123405 A1* | 5/2012 | Moua ............... A61B 42/10 606/33 |
| 2012/0143293 A1 | 6/2012 | Mauch et al. |
| 2012/0151165 A1 | 6/2012 | Conley et al. |
| 2012/0157989 A1 | 6/2012 | Stone et al. |
| 2012/0184983 A1 | 7/2012 | Chang et al. |
| 2012/0191084 A1 | 7/2012 | Davison et al. |
| 2012/0253343 A1 | 10/2012 | McClurken et al. |
| 2013/0110108 A1* | 5/2013 | Davison ............ A61B 18/1402 606/45 |
| 2013/0178845 A1* | 7/2013 | Smith ................ A61B 18/18 606/33 |
| 2013/0178852 A1 | 7/2013 | Allen et al. |
| 2014/0005666 A1* | 1/2014 | Moua ............... A61B 17/295 606/45 |
| 2014/0276770 A1* | 9/2014 | Ellman ............. A61B 18/1477 606/34 |
| 2014/0276772 A1* | 9/2014 | Batchelor ......... A61B 18/1442 606/34 |

FOREIGN PATENT DOCUMENTS

| | | |
|---|---|---|
| WO | WO2010/141417 | 12/2010 |
| WO | 2014/133633 | 9/2014 |

* cited by examiner

MULTIPURPOSE ELECTROSURGICAL DEVICE

CROSS-REFERENCE

This Non-Provisional Utility application claims benefit to U.S. Provisional Application No. 62/208,931, filed Aug. 24, 2015, entitled "MULTIPURPOSE ELECTROSURGICAL DEVICE" incorporated herein by reference.

BACKGROUND

This disclosure relates generally to the field of medical devices, systems and methods for use in surgical procedures. More specifically, this disclosure relates to electrosurgical devices, systems and methods that provide for cutting, coagulation, hemostasis and sealing of bodily tissues including bone with a single electrosurgical device.

Electrosurgery includes such techniques as cutting, coagulation, hemostasis, and/or sealing of tissues with the aid of electrodes energized with a suitable power source such as an electrosurgical unit including a power generator. Typical electrosurgical devices apply an electrical potential difference or a voltage difference between an active electrode and a return electrode on a patient's grounded body in a monopolar arrangement or between an active electrode and a return electrode on the device in bipolar arrangement to deliver electrical energy to the area where tissue is to be affected. The electrosurgical device are typically held by the surgeon and connected to the power source, such as the electrosurgical unit, via cabling.

In one example, an electrical signal, such as voltage, is applied either as a train of high frequency pulses or as a continuous signal typically in the radiofrequency (RF) range. The signals could include a set of parameters, such as power or voltage level parameters, waveform parameters such as frequency, pulse duration, duty cycle, and other signal parameters. For example, a surgeon could use a monopolar electrosurgical device to cut tissue and control bleeding. Tissue could be cut using a first RF signal having a set of parameters and bleeding could be controlled using a second RF signal having another set of parameters. The surgeon could also use a bipolar electrosurgical device for hemostatic sealing of the tissue that would employ a third RF signal having a unique set of parameters.

Historically, two distinct electrosurgical devices, one monopolar and the other bipolar, were use to perform different functions in surgery, such as tissue cutting and tissue sealing. For example, a surgeon would use a monopolar electrosurgical device to cut tissue and control bleeding and use a bipolar electrosurgical device for hemostatic sealing of the tissue. When these different functions were performed during a surgical procedure, surgeons would switch between different devices. Switching between devices can lead to undesirable effects such as longer procedure times, higher costs, and an increased likelihood of inaccuracy or imprecision.

To address these issues, some electrosurgical devices capable of operating in both monopolar and bipolar mode have been developed. Several such electrosurgical device are described, for example, in U.S. Pat. No. 8,632,533 to Greeley, et al., U.S. Patent Application Publication No. 2012/000465 to Conley, et al., U.S. Patent Application Publication No. 2011/0178515 to Bloom et al., each assigned to the assignee of the present disclosure and incorporated by reference herein in their entireties to the extent they are not inconsistent with the present disclosure.

Several devices that have been developed include a hand piece having two electrodes. These devices can be configured as bipolar electrodes connected to a source of bipolar power to operate in a bipolar mode via input cables, for example to seal tissue. To operate the same two-electrode device in a monopolar mode, for example to cut tissue and control bleeding, one of the two electrodes selectively deactivated and the other of the two electrodes coupled to a source of monopolar power. During monopolar operation, the monopolar electrode of the device may be used in conjunction with a ground pad dispersive electrode placed on a patient, which is commonly known as a patient return electrode or grounding pad. In this manner, the dual function device may provide treatment to tissue utilizing one or both electrodes depending upon the desired tissue treatment.

Despite having the ability to perform different functions with a single device, when monopolar function is desired only one of the two electrodes of the device are utilized. The deactivated second electrode may obstruct the view of the surgeon during the monopolar operation. Furthermore, the deactivated electrode may prevent the monopolar electrode from entering smaller spaces or tissue areas that could otherwise be accessed if the unused electrode was not exposed. Devices where the problem of an obstructive deactivated second electrode has been addressed may not provide for a robust electrode/tissue interface if the device is used in bipolar mode.

Multifunction electrosurgical devices also create additional concerns for surgeons. For example, multifunction devices generally have dedicated inputs in the form of wires and cords corresponding for each function that adds weight to the electrosurgical device and decreases flexibility of the input cable, which can result in hand stain for the surgeon. A monopolar device may include an input cable having at least two wires for electrical power, and a bipolar device may include an input cable having at least three wires for electrical power and a fluid delivery tube. A multifunction device may include an input cable having at least five cables and a fluid delivery tube. Additionally, each of these functions may require an activation mechanism, such as a pushbutton on the handpiece, a footswitch, a mouth-switch, or other activation mechanism that may cause confusion for the surgeon or may be inadvertently selected. As functions are added to electrosurgical devices, these concerns will become more pronounced and diminish from the utility of the device.

SUMMARY

This summary is provided to introduce a selection of concepts in a simplified form that are further described below in the Detailed Description.

The disclosed electrosurgical devices can be operated with electrosurgical units that can detect which activation switch on the device is selected. One such electrosurgical unit is available under the trade designation AEx from Medtronic Advanced Energy of Portsmouth, N.H. The electrosurgical unit, in one example, uses a topology of circuit elements, such as a resistor ladder, to determine which activation switch of a connected electrosurgical device is selected. In the example, the generator can provide RF signals corresponding with at least three functions such as hemostatic sealing in bipolar configuration, cutting in monopolar configuration, and coagulation in monopolar configuration.

The devices of this disclosure can include the ability to perform these at least three different functions while reducing or eliminating the adverse issues of previous electrosurgical devices. Having three functions on a single, multipurpose electrosurgical device eliminates or reduces interruption in changing devices that can reduce surgical time. The bipolar electrodes used in bipolar mode do not obstruct view or unnecessarily prevent the monopolar electrode blade from entering smaller spaces or tissue areas. Further, the co-planar arrangement of the bipolar electrodes provides for a robust electrode/tissue interface in bipolar mode.

Further, the disclosed electrosurgical devices reduce what would be three wires (a wire corresponding with each function) in a cable from the electrosurgical unit to the to device to a single conductor. The examples of the electrosurgical device can perform the three functions using only two buttons. Also, the example electrosurgical devices are configured so as not to activate unused electrodes. The features increase the ergonomics of multipurpose electrosurgical devices.

Eliminating wires to the device reduces weight and increases flexibility of the cable, which reduces strain on the surgeon's hand and wrist. Eliminating buttons for each function reduces confusion for the user. And reducing or eliminating the possibility of inadvertent activation provides for less chance of inadvertent damage to tissue or the device. Other advantages are contemplated.

In one aspect, the disclosure relates to a multipurpose electrosurgical device that is configurable in a bipolar mode and a monopolar mode using a three-conductor electrical input. The device includes a switching mechanism that provides signals corresponding with a first function, such as a cut function, and a second function, such as a coagulation function, in a monopolar mode. The switching mechanism also provides a signal corresponding with a third function, such as a hemostatic sealing function, in a bipolar mode. In one example of this device, the switching mechanism includes only two switches to provide three functions.

In another aspect the disclosure relates to an electrosurgical device that can be coupled to an electrosurgical unit. The electrosurgical device includes a handpiece, a switching mechanism, a first electrode tip and a second electrode tip. The first electrode tip is fixedly coupled to the handpiece and selectively coupled to the switching mechanism. The second electrode tip is transitionable between a retracted position and a protracted position with respect to the handpiece. The second electrode tip is selectively coupled to the switching mechanism in the protracted position, and the first electrode tip is selectively coupled to the switching mechanism when the second electrode tip is in the retracted position. In one example, the first electrode tip includes a monopolar electrode and the second electrode tip includes bipolar electrodes.

In another aspect, the disclosure relates to an electrosurgical device that can be coupled to an electrosurgical unit. The electrosurgical device includes a first conductor, such as switch input, that can be coupled to an energy detection system in an electrosurgical device and a second conductor, such as an active input, that can be coupled to a source of RF energy. The second conductor is operably configured to be coupled to an active electrode, such as an active bipolar electrode or monopolar electrode via a switch mechanism. The monopolar electrode is activated at a first monopolar RF energy level when the switch mechanism is used to electrically couple the first and second conductors via a first circuit element. Also, the monopolar electrode is activated at a second monopolar RF energy level when the switch mechanism is used to electrically couple the first and second conductors via a second circuit element. Further, the bipolar electrode is activated at a bipolar RF energy level when the switch mechanism is used to electrically couple the first and second conductors in a bipolar mode.

In still another aspect, the disclosure relates to a method of selectively configuring an electrosurgical device for use in a bipolar mode and a monopolar mode. The method includes configuring the device in a monopolar such as by disposing a monopolar electrode blade distal most on the device. In one example, disposing the monopolar electrode blade includes attaching the monopolar blade to a handpiece. In another example, disposing the monopolar electrode blade includes retracting bipolar electrodes into the handpiece. The method further includes activating the monopolar electrode blade with a first RF energy, such as an energy corresponding with the cut function, using a first switch. The monopolar electrode blade is activated with a second RF energy, such as an energy corresponding with the coagulation function, using a second switch. The method includes configuring the device in a bipolar mode such as by attaching or extending bipolar electrodes distally from the electrosurgical device. A third function, such as hemostatic sealing, can be affected by closing one of the switches.

DETAILED DESCRIPTION

Figure 1:
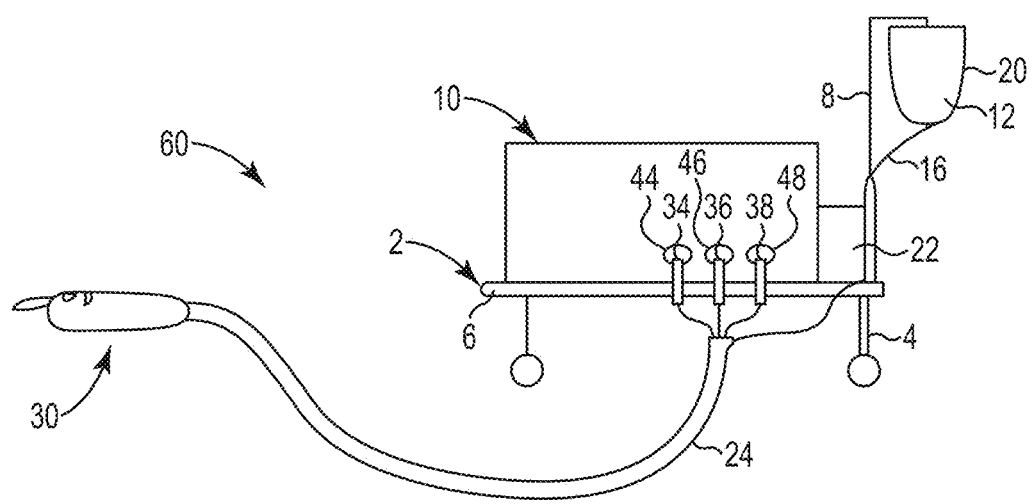
FIG. 1 is a front view of an embodiment of a system according to the present disclosure including an example electrosurgical unit in combination with a fluid source and handheld electrosurgical device.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

FIG. 1 illustrates a front view of one example of a system 60 that includes an electrosurgical unit 10 in combination with a fluid source 20 and an example handheld electrosurgical device 30. The device 30 can be a multipurpose device configurable for use in cutting and sealing, including electrocautery, coagulation, and hemostatic sealing of tissue including bone and configurable for use in both a monopolar and a bipolar mode.

The system 60 can be carried on a movable cart 2 having a support member 4 comprising a hollow cylindrical post which includes a platform 6 comprising a pedestal table to provide a flat, stable surface for location of the electrosurgical unit 10. Cart 2 can include a pole 8 having a height that can be adjusted by sliding the pole 8 up and down. Fluid source 20 can be supported at the top of pole 8.

Fluid source 20 may comprise a bag of fluid from which fluid 12 may flow through a drip chamber 14, to delivery tubing 16 and to handheld electrosurgical device 30. In one example, the fluid 12 includes saline and can include physiologic saline such as sodium chloride (NaCl) 0.9% weight/volume solution. Saline is an electrically conductive fluid, and other suitable electrically conductive fluids can be used. In other examples, the fluid may include a nonconductive fluid, such as deionized water, which may still provide advantages over using no fluid and may support cooling of portions of electrosurgical device 30 and tissue or reducing the occurrence of tissue sticking to the electrosurgical device 30.

The fluid delivery tubing 16 in the example passes through pump 22 to convey fluid to the electrosurgical device 30 and control fluid flow. Pump 22 in one example is a peristaltic pump such as a rotary peristaltic pump or a linear peristaltic pump. A peristaltic pump can convey the fluid through the delivery tubing 16 by way of intermittent forces placed on the external surface of the delivery tubing. Peristaltic pumps are often applied during use of the electrosurgical device 30 because the mechanical elements of the pump places forces on the external surface of the delivery tubing and do not come into direct contact with the fluid, which can reduce the likelihood of fluid contamination. Other examples of system 60 might not include a pump, and fluid can be is provided to the electrosurgical device 30 via gravity.

The example electrosurgical unit 10 is configured to provide both monopolar and bipolar radio-frequency (RF) power output to a specified electrosurgical instrument such as electrosurgical device 30. In one example, the electrosurgical unit 10 can be used for delivery of RF energy to instruments indicated for cutting and coagulation of soft tissue and for delivery of RF energy concurrent with fluid to instruments indicated for hemostatic sealing and coagulation of soft tissue and bone. In one example, the electrosurgical unit 10 is capable of simultaneously powering specified monopolar and bipolar electrosurgical instruments but may include a lock out feature preventing both monopolar and bipolar output from being simultaneously activated.

During monopolar operation of electrosurgical device 30, a first electrode, often referred to as the active electrode, is provided with electrosurgical device 30 while a second electrode (not shown), often referred to as the indifferent or neutral electrode, is provided in the form of a ground pad dispersive electrode located on a patient. For example, the ground pad dispersive electrode is typically on the back, buttocks, upper leg, or other suitable anatomical location during surgery. In such a configuration, the ground pad dispersive electrode is often referred to as a patient return electrode. An electrical circuit of RF energy is formed between the active electrode and the ground pad dispersive electrode through the patient.

During bipolar operation of electrosurgical device 30, a second electrode, often referred to as the return electrode providing a second electrical pole, is provided as part of the device 30. The ground pad dispersive electrode is not used. An electrical circuit of RF energy is created between the first and second poles of the device 30. The current no longer flows through the patient's body to the ground pad dispersive electrode, but rather through a localized portion of tissue between the poles of the device 30.

The electrosurgical device 30 in the example is connected to electrosurgical unit 10 via cable 24. Cable 24 includes first plug 34, second plug 36, and third plug 38 that connect with first receptacle 44, second receptacle 46, and third receptacle 48 on the electrosurgical device, respectively. In one example, the first receptacle 44 corresponds with a switch receptacle, the second receptacle 46 corresponds with an active electrode receptacle, and the third receptacle 48 corresponds with a return electrode receptacle. When electrosurgical unit 10 may be used in monopolar mode, an additional cable may connect a ground pad electrode to a ground pad receptacle of the electrosurgical unit 10. In some examples, delivery tubing 16 and cable 24 are combined to form a single cable.

The features of electrosurgical unit 10 described are for illustration, and the electrosurgical units suitable for use with device 30 may include some, all, or other features than those described below. In one example, the electrosurgical unit is capable of operating in monopolar and bipolar modes as well as multiple functions with a mode such as a monopolar cutting function and a monopolar coagulation function.

In some examples, a monopolar device is capable of performing a monopolar hemostasis or tissue sealing function. In the monopolar cutting function, monopolar RF energy is provided the device 30 at a first power level and/or a first waveform (collectively first RF energy level). For example, RF energy for a cut function may be provided at a relatively low voltage and a continuous current (100% on, or 100% duty cycle). Nominal impedance can range between 300 to 1000 ohms for the cutting function. At a power setting of 90 Watts for cutting, voltage can range from approximately 164 to 300 volts root mean square (RMS). In the monopolar coagulation function, monopolar RF is energy is provided to the electrode at a second power level and/or second waveform (collectively second or coagulation RF energy level) that is different than at least one of the first power level or the first waveform. For example, RF energy for a coagulation function may be provided at a relatively higher voltage than the cut voltage and with a pulsed current, such as 1% to 6% on and 99% to 94% off, respectively (or 1% to 6% duty cycle). Other duty cycles are contemplated. The electrosurgical unit 10 in the bipolar mode may provide bipolar RF energy at a third power level and/or third waveform (collectively third RF energy level) to the device 30 along with a fluid for a (generally low voltage) hemostasis or tissue sealing function that may be same as or different than the cutting and coagulation RF settings provided to the device 30 for the cut function or the coagulation function. In one example, hemostatic sealing energy can be provided with a continuous current (100% duty cycle). Nominal impedance can range between 100 to 400 ohms for the hemostatic sealing function. At a power setting of 90 Watts for hemostatic sealing, voltage can range from approximately 95 to 200 volts RMS.

In one example, the unit 10 provides RF energy to the active electrode as a signal having a frequency in the range of 100 KHz to 10 MHz. Typically this energy is applied in the form of bursts of pulses. Each burst typically has a duration in the range of 10 microseconds to 1 millisecond. The individual pulses in each burst typically each have a duration of 0.1 to 10 microseconds with an interval between pulses of 0.1 to 10 microseconds. The actual pulses are often sinusoidal or square waves and bi-phasic, that is alternating positive and negative amplitudes. Several other features are described in U.S. Pat. No. 8,323,276, to Palanker et al., and incorporated by reference herein in its entirety to the extent it is not inconsistent with the present disclosure.

The electrical surgical unit 10 includes a power switch to turn the unit on and off and an RF power setting display to display the RF power supplied to the electrosurgical device 30. The power setting display can display the RF power setting numerically in a selected unit such as watts.

The example electrosurgical unit 10 includes an RF power selector comprising RF power setting switches that are used to select or adjust the RF power setting. A user can push one power setting switch to increase the RF power setting and push the other power setting switch to decrease the RF power setting. In one example, power setting switches are membrane switches, soft keys, or as part of a touchscreen. In another example, the electrosurgical unit may include more than one power selectors such as a power selector for monopolar power selection and a power selector for bipolar power selection. The electrosurgical unit can also include an RF power activation display having an indicator light that can illuminate when the RF power is activated either via a hand switch on the device 30, a foot switch, or other switch.

The example electrosurgical unit 10 also includes fluid flow rate setting display and flow rate setting selector. The display can include indicator lights, and the flow rate selector can include switches. Pushing one of the flow rate switches selects a fluid flow rate, which is than indicated in display.

Device 30 can be primed with fluid 12 prior to beginning a surgical procedure. Priming may be desirable to inhibit activating the RF power without the presence of fluid 12. The example electrosurgical device 10 can also include a priming switch 70 to initiate priming of the device 30. In one example, the depressing the priming switch will operate the pump for a predetermined amount of time or fluid flow to prime the device 30. After the device 30 has been primed, the pump 22 may shut off automatically.

Figure 2:
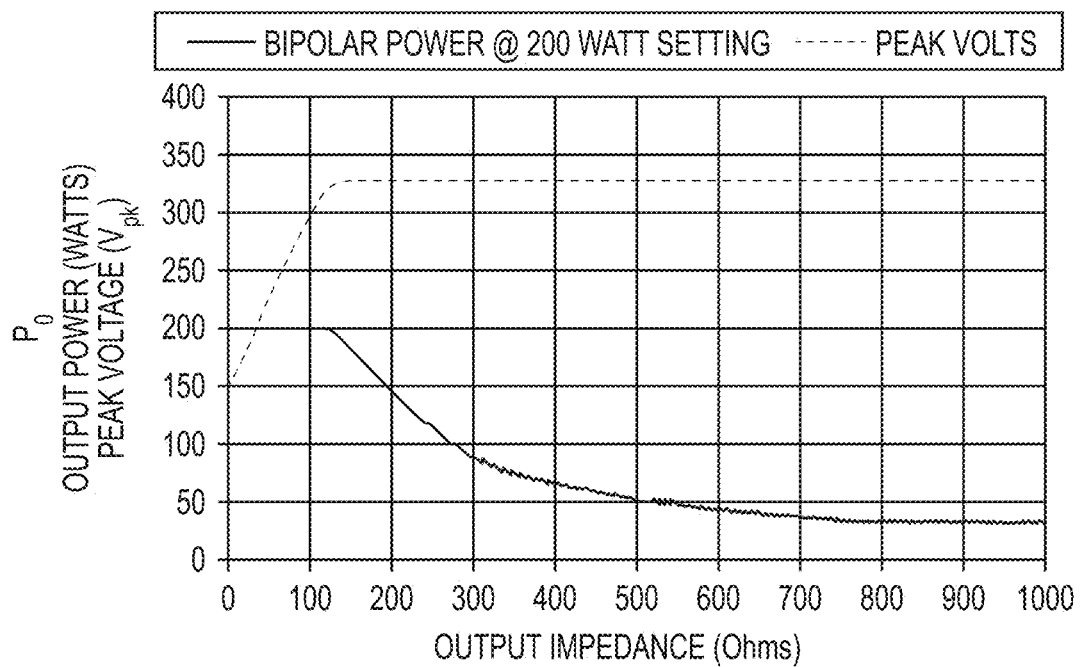
FIG. 2 is a graph of a bipolar radio frequency power output versus impedance for the electrosurgical unit of FIG. 1.

FIG. 2 illustrates an example bipolar RF power output versus impedance for the electrosurgical unit 10. Impedance Z is indicated in units of ohms on the X-axis and output power $P_O$ is indicated in units of watts on the Y-axis. The bipolar power (RF) setting $P_S$ for the electrosurgical device 10 is selected at 200 watts in the example. As illustrated, the power output $P_O$ for the selected power setting $P_S$ generally remains constant for an impedance Z between the low impedance cut-off of 30 ohms and the high impedance cut-off of 120 ohms. Below an impedance Z of 30 ohms, the output power $P_O$ for the selected power setting $P_S$ will decrease; and above an impedance Z of 120 ohms, the output power $P_O$ for the selected power setting $P_S$ will increase.

Electrosurgical unit 10 can be configured to include control of the pump 22. In this example, the speed of the pump 22, and the fluid throughput, can be predetermined based on input variables such as the RF power setting and the fluid flow rate setting. In one example, the pump 22 can be integrated with the electrosurgical unit 10.

Figure 3:
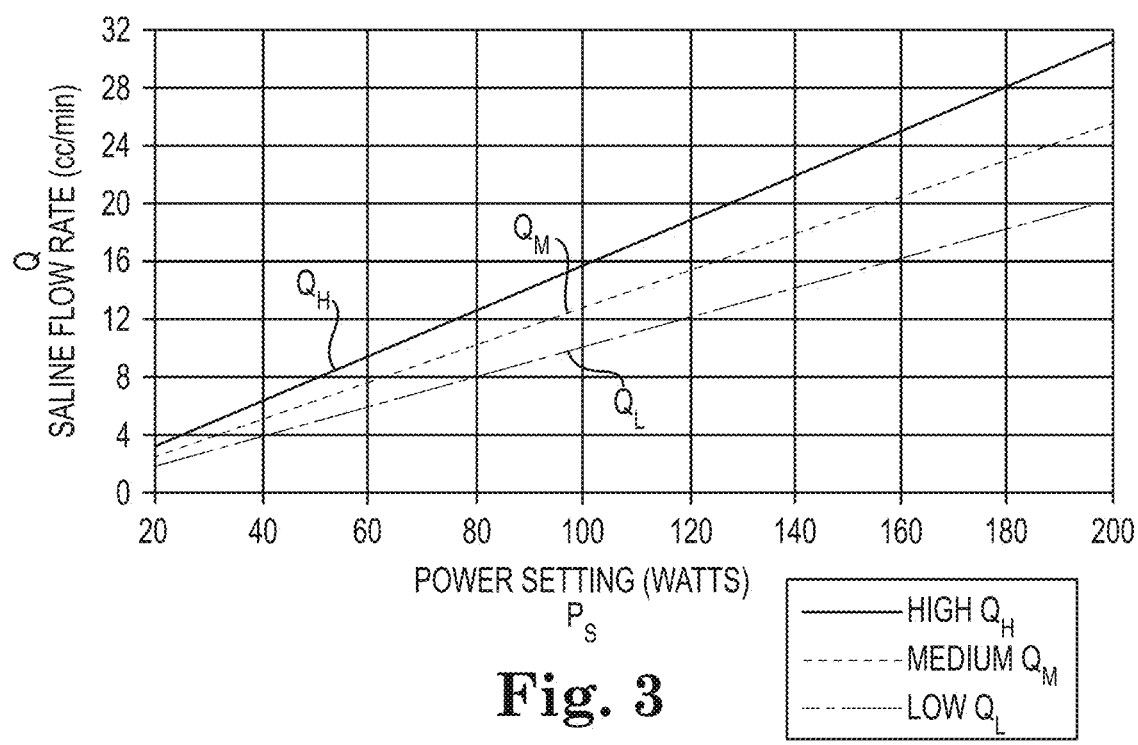
FIG. 3 is a graph of illustrating a relationship of radio frequency power setting to fluid flow rate.

FIG. 3 illustrates an example functional relationship of fluid flow rate Q in units of cubic centimeters per minute (cc/min) on the Y-axis and RF power setting $P_S$ in units of watts on the X-axis. While not being bound to a particular theory, the relationship between the variables can be configured to inhibit undesired effects such as tissue desiccation, electrode sticking, smoke production, char formation, and other effects while not providing a fluid flow rate Q at a corresponding RF power setting $P_S$ not so great as to disperse too much electricity and or overly cool the tissue at the electrode/tissue interface. Electrosurgical unit 10 is configured to increase the fluid flow rate Q generally linearly with an increasing RF power setting $P_S$ for each of the three fluid flow rate settings of low, medium, and high corresponding to $Q_1$, $Q_2$, $Q_3$, respectively.

In examples of system 60 that do not include a pump for fluid 12, there may not be a preset functional relationship between fluid flow rate Q and RF power setting $P_S$ stored in electrosurgical unit 10. Rather than the fluid flow rate Q being automatically controlled by the electrosurgical unit 10 based on RF power setting $P_S$, the fluid flow rate Q may be manually controlled, such as by the user of the device 30 or another clinician with a roller or pinch clam or other clamp provided with system 60 and configured to act upon and compress the tubing 16 to control flow.

While multipurpose electrosurgical surgical device 30 is described with reference to electrosurgical unit 10 and other elements of system 60, it should understood the description of the combination is for the purposes of illustrating system 60. It may be possible to use the multipurpose electrosurgical device 30 in other systems or the electrosurgical unit 10 may be used with other electrosurgical devices.

Figure 4:
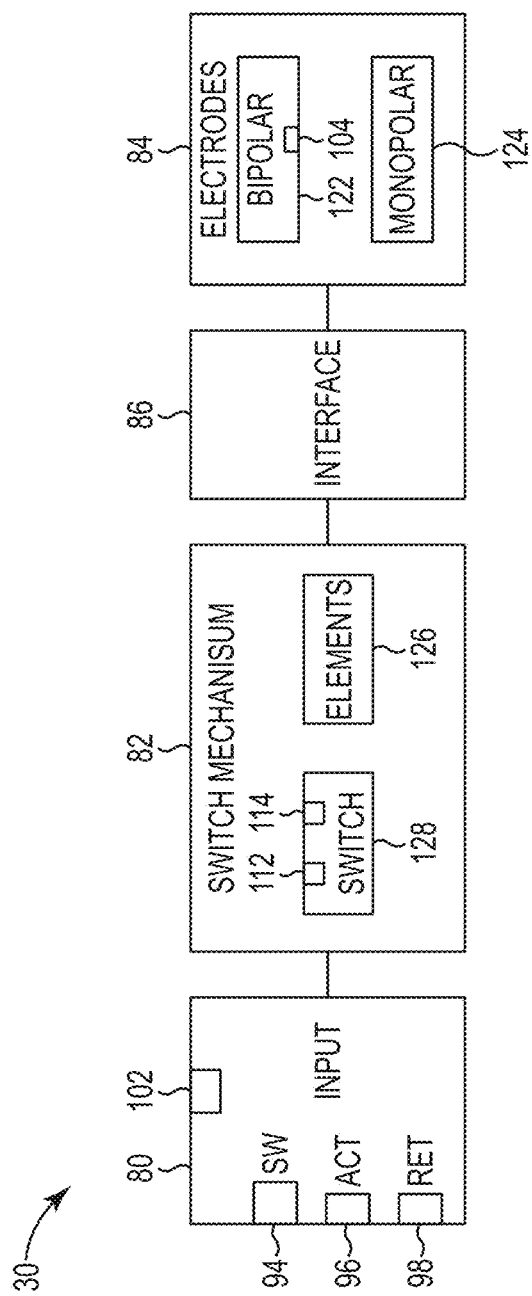
FIG. 4 is a block diagram of the example handheld electrosurgical device of FIG. 1.

FIG. 4 illustrates a block diagram of the exemplary multipurpose electrosurgical device 30 constructed in accordance with the disclosure. The device 30 includes an cable input 80 that includes electrical connections to electrically communicate with the electrosurgical unit 10, a switching mechanism 82 to select a particular mode and function of the device, electrode tips 84 to deliver RF energy to the tissue, and an interface 86 to couple the electrode tips 84 to the switching mechanism 82. For example, device 30 may be operable in a bipolar mode and monopolar mode and may include two functions, such as a cut function and a coagulation function, in the monopolar mode.

In one example, the device 30 receives three electrical connections at the cable input 80 including a switch input 94, an active input 96, and a return input 98 at the distal end 88 of the cable 24 that correspond with first plug 34, second plug 36, and third 38 at the proximal end of the cable 24. In one example, the device receives only three electrical connections 94, 96, 98. The cable input 80 can also include a fluid input 102 that can be configured to be in fluid communication with the delivery tubing 16 to receive fluid 12 at the device 30.

The electrode tips 84 include bipolar electrodes 122 and a monopolar electrode 124, such as an electrode blade. The bipolar electrodes 122 are selected to configure the device 30 to operate in bipolar mode, and the monopolar electrode blade 124 is selected to configure the device in monopolar mode. The electrode tips 84 can include a fluid port 104 in fluid communication with the fluid input 102 when the bipolar electrode 122 is selected.

In one example, the device includes two or more interchangeable and removable electrode tips 84. For example, interchangeable and removable electrode tips can include one or more bipolar electrode tips 122 and one or more monopolar electrode blades 124 of various sizes and configurations depending on the surgical application or other preferences such as longer electrodes, shorter electrodes, wider electrodes, electrodes of a specific shape, and so on. When a bipolar electrode tip is attached to the interface 86 and electrically coupled to the cable input 80, the device 30 is operated in a bipolar mode and can receive bipolar RF energy from the electrosurgical unit 10. When a monopolar electrode is attached to the interface 86 and electrically coupled to the cable input 80, the device 30 is operable in monopolar mode and can receive monopolar RF energy from the electrosurgical unit 10. In some examples, the device 30 can include a holder to receive the unused electrode tip or tips so as to be readily available when the operator wishes to switch modes.

In another example, the electrode tips 84 are attached to the device 30 and not removable. The electrode tips 84 can be positioned with respect to the device 30 to be selectively operable in either a bipolar or monopolar mode. For example, if the surgeon wishes to operate the device 30 in a bipolar mode, bipolar electrodes 122 are positioned to be on the distal most end of the device. If instead the surgeon wishes to operate the device 30 in a monopolar mode, monopolar electrode blade 124 is positioned to be on the distal most end of the device.

The switch mechanism 82 is electrically coupled to the cable input 80 including the switch input 94, active input 96, and return input 98, and selectively applies RF electrical energy depending on the mode chosen via the electrode tips 84. For example, the switch mechanism 82 can include circuit elements 126 used in cooperation with the electrode tips 84 to detect whether the device 30 is to be operated in bipolar mode or in monopolar mode and to select the particular function in monopolar mode. The switch mechanism 82 includes switch 128 to selectively apply RF energy received from the cable input 80 to the electrode tips 84 depending on the mode and function selected.

In one example, the switch mechanism 82 provides a first signal, such as a cut signal, to the electrosurgical unit 10 to receive monopolar RF energy for a first function, such as the cut function, if the device 30 is configured in a monopolar mode. The switch mechanism 82 can also provide a second signal, such as a coagulation signal, to the electrosurgical unit 10 receive monopolar RF energy for a second function, such as the coagulation function, if the device 30 is configured in a monopolar mode. Additionally, the switch mechanism 82 can provide a third signal, such a bipolar signal, to electrosurgical unit 10 receive bipolar RF energy if the device 30 is configured in a bipolar mode.

In one example, the switch 128 includes two switches 112, 114, where one switch 112 selects the cut function and activates the monopolar electrode blade 124 with the corresponding monopolar RF energy for the cut function and the other switch 114 selects the coagulation function and activate the monopolar electrode blade 124 with the corresponding monopolar RF energy for the coagulation function. One or both of the switches 112, 114 can be used to activate the bipolar electrodes 122 with the bipolar RF energy.

The interface 86 includes electrical contacts to electrically couple the switch mechanism 82 to the electrode tips 84. In one example, the interface includes at least four electrical contacts, as described below such as four electrical contacts for removable and interchangeable electrode tips 84 and five electrical contacts for non-removable electrode tips 84. Additionally, the interface may include a fluid coupling to couple the fluid input 102 to the fluid port 104 when the device 30 is configured in bipolar mode. The interface 86 can also include features to hold the electrode tips 84 in position during operation, such as a mechanical connection that can releasably lock the electrode tips 84 in position while in either the monopolar mode or bipolar mode.

Figure 5:
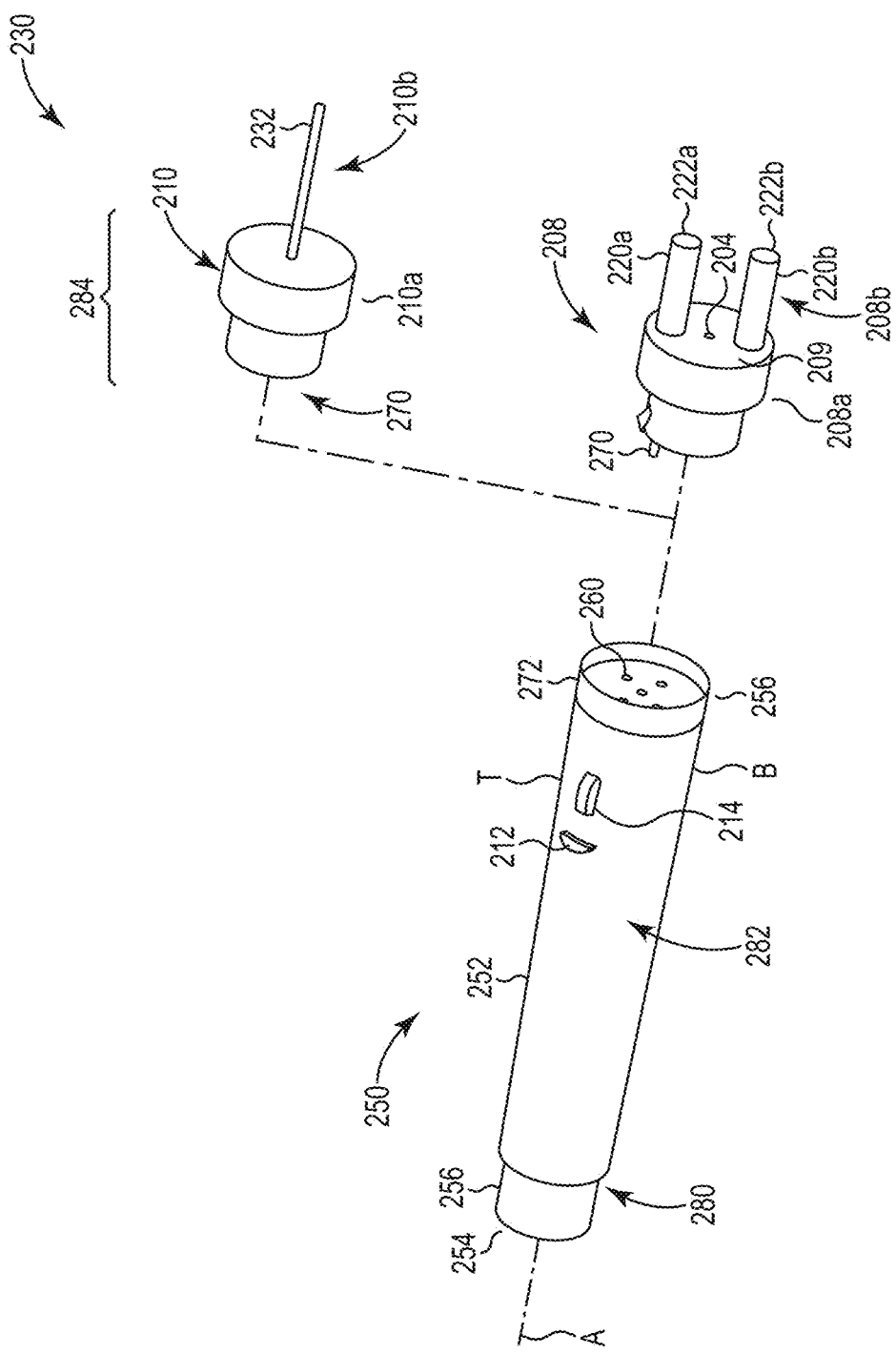
FIG. 5 is a perspective view of an example electrosurgical device of FIG. 4 having interchangeable monopolar and bipolar attachment tips.

FIG. 5 illustrates an exemplary multipurpose electrosurgical device 230 constructed in accordance with the electrosurgical device 30 described above and on longitudinal axis A. The device 230 includes a handpiece 250 and at least two electrode tips 284 including a bipolar electrode tip 208 and monopolar electrode tip 210. In one example, the handpiece 250 includes the cable input 80, switch mechanism 82, and interface 86 described above. The electrode tips 284 can correspond with electrode tips 84 described above. The bipolar electrode tip 208 is connected to the handpiece 250 to operate the device in bipolar mode, and the monopolar tip 210 is connected to the handpiece 250 to operate the device in the multiple functions of the monopolar mode.

The handpiece 250 includes a handle 252, a proximal end 254, and an interface end 256. The proximal end 254 includes a cable input 280 configured to receive the distal end 88 of cable 24. For example, the proximal end 254 receives cable for electrical connections 94, 96, 98 located within the handpiece 250 as well as fluid delivery tubing 16. In some examples, the proximal end 254 can includes a strain relief 256 attached to the distal end 88 of the cable 24.

Handpiece 250 may be configured to enable a user of device 230 to hold and manipulate device 230 between the thumb and index finger like a writing instrument or an electrosurgical pen. Handpiece 250 may comprise a sterilizable, rigid, electrically insulative material, such as a synthetic polymer (e.g., polycarbonate, acrylonitrile-butadiene-styrene). The handle 252 can include a lower surface, or bottom B, and an upper surface, or top T.

The interface end 256 can be configured on the distal end of the handpiece 250 and include electrical contacts 260 to mate with electrical contacts 270 on the electrode tips 284. The interface end 256 can also include a sleeve 272 extending axially from the handpiece 250 configured to receive the edges of the electrode tips 284 and protect the electrical contacts 260, 270 from exposure during operation. The interface end 256 can be configured to guide the electrode tips 284 to mate with the electrical contacts 260 with the corresponding electrical contacts 270 on the electrode tips 284 to facilitate connection. The interface end 256 can also include a mechanical fastening system to removably attach the handpiece 250 to the electrode tips 284. In one example, the sleeve 272 can provide an interference or frictional fit against the electrode tips 284. The surgeon can remove or replace the electrode tip 284 by tugging apart the handpiece 250 from the electrode tip 284. In another example, the sleeve 272 can include a first portion of clip mechanism that mates with a second portion of a clip mechanism on the electrode tips 284. In this example, the second portion of the clip mechanism (or, in an alternative example, the first portion of the clip mechanism) can be squeezed to allow the electrode tip 284 to be pulled from the sleeve 272. The sides of the squeezable portion of the clip mechanism can include grips to aid in locating the clip mechanism.

The electrode tips 284 can include a body portion and an electrode portion extending distally from the body portion. The body portion can be configured to fit against the interface end 256 of the handpiece 250. In one example, the body portion of the electrode tips can include electrical contacts 270 to mate with electrical contacts 260 on the interface end 256. The body portion can be formed from a material similar to the handpiece 250, or other material, such that the surgeon can grasp the body portion instead of the electrode portion when installing or removing the electrode tips 284 from the handpiece 250. The electrode tips 284 can include electrical conductors or circuit elements and electrical conductors that, when coupled to the switch mechanism 82 included in the handpiece 250, select and transfer the appropriate electrical energy to from the electrosurgical unit 10 to the electrode portion.

The bipolar electrode tip 208 includes body portion 208a and electrode portion 208b extending distally from a distal face 209 of the body portion 208a. The body portion 208a can include an internal fluid lumen in communication with delivery tubing 16 and having a fluid outlet port, such as fluid outlet port 204 on distal face 209. Electrode portion 208b comprises two electrode tips 220a, 220b for treating tissue. Electrode tips 220a, 220b extend from the body portion 208a and, in the example, include blunt, rounded tips having distal-most electrode ends 222a, 222b, respectively. Distal-most electrode ends 222a, 222b may provide smooth continuous surfaces and in one example are devoid of points or edges. Electrode tips 220a, 220b may be configured to optimize tissue sealing or coagulation in conjunction with delivery of fluid or for a particular application or anatomical geometry. In one example, the electrode tips 220a, 220b may be removable from the body portion 208a and selectable to suit a particular design configuration or application.

The monopolar electrode tip 210 includes body portion 210a and electrode portion 210b extending distally from a distal face 211 of the body portion 210a. The monopolar electrode portion 210b includes a blade tip 232 that may taper to form a sharp or razor-like blade. In one example, the monopolar electrode tip 210 can include an interchangeable electrode portion 210b that can be removed from the body portion 210a. The interchangeable electrode portion 210b can be selected to include a particular design configuration suitable for the application. In one example, the interchangeable electrode portion 210b can include a blade-like configuration. In another example, the interchangeable electrode portion 210b can include a blunt tip. The monopolar electrode portion 210b can include a conductor electrically coupled to and proximal to the blade tip 232 that is configured to mate with a conductor in the body portion 210a. Other configurations are contemplated including multiple monopolar electrodes.

The handpiece 250 includes a switch mechanism 282 to complete an electrical circuit between the conductors of cable input 280. In one example, the switch mechanism 282 includes push buttons 212 and 214 projecting from the upper surface or top T of the handle 252. Push buttons 212, 214 comprise hand switch assemblies for forming a closed circuit that can be sensed by an electrosurgical unit, such as electrosurgical unit 10, to selectively provide at least three variations of monopolar power and bipolar power.

For example, when the device 230 is configured in monopolar mode, such as monopolar tip 210 is electrically coupled to the interface end 256, one pushbutton 212 is depressed so monopolar RF energy corresponding with the cut function is provided to the blade tip 232. Also, when the device 230 is configured in monopolar mode, the other pushbutton 214 is depressed so monopolar RF energy corresponding with the coagulation function is provided to the blade tip 232.

When the device 230 is configured in bipolar mode, such as bipolar tip 208 is electrically coupled to the interface end 256, one or both of pushbuttons 212, 214 can be depressed to select bipolar RF energy corresponding with the bipolar hemostatic sealing function and provide bipolar RF energy to the electrode tips 220a, 220b. In an example where just one pushbutton activates the bipolar tip 208, the other pushbutton can leave the electrode tips 220a, 220b inactive.

Figure 6:
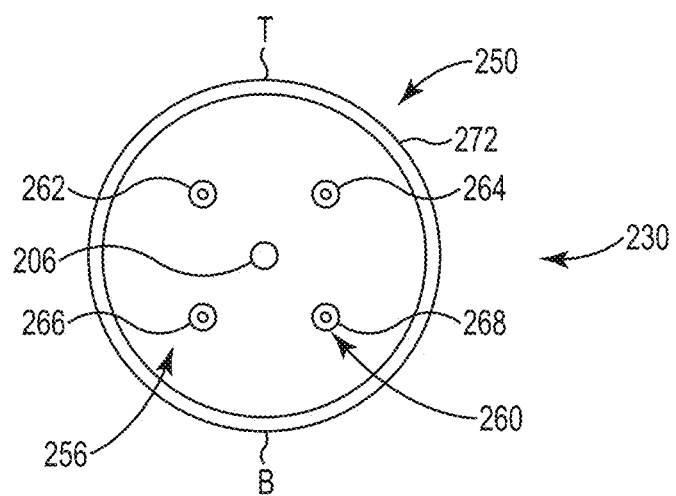
FIG. 6 is an end view of the electrosurgical device of FIG. 5 illustrating an interface configured to couple to the interchangeable monopolar and bipolar attachment tips.

FIG. 6 illustrates the interface end 256 of device 230 as viewed on axis A. Interface end 256 in the example includes four exposed female electrical connections 262, 264, 266, 268 that can correspond with one or more male electrical connections on the electrode tips 208, 210. The one or more electrode connection on electrode tip are electrically connected to electrode tips 220a, 220b via one or more internal conductors. Similarly, two or more electrical conductors on monopolar electrode tip 210 are electrically connected to blade tip 232 via internal conductors. Alternatively, the interface end 256 can include male conductors that are configured to mate with female connectors on the electrode tips 208, 210. The male/female connections can serve to hold the electrode tips 208, 210 in place with respect to the handpiece 250. If other electrical contacts are used to transfer electrical energy from the handpiece 250 to the electrode tips 208, 210, the handpiece 250 may include a mechanical locking mechanism to hold the electrode tips 208, 210 in place. The interface end 256 can also include fluid connection 206 in fluid communication with delivery tubing 16 that is fluidly coupleable to a fluid lumen in the bipolar electrode tip 208. The monopolar electrode tip 210 can include a plug configured to seal the fluid connection 206.

Figure 7:
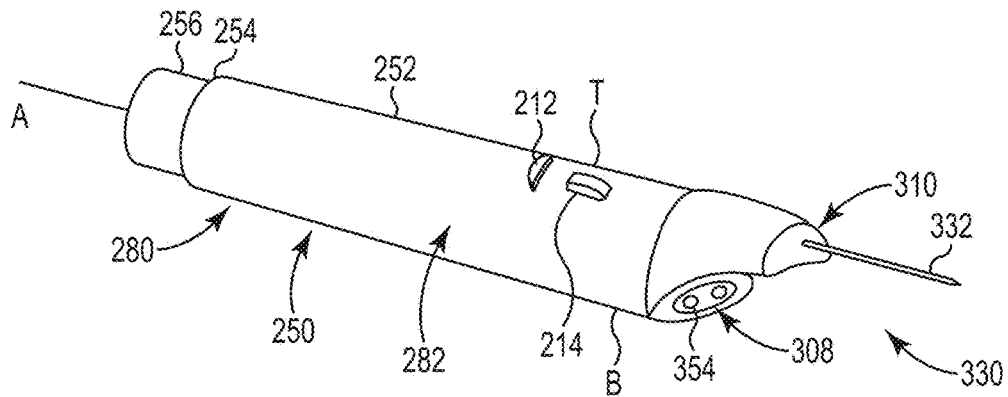
FIG. 7 is a perspective view of another example of the handheld electrosurgical device of FIG. 5 configured for use in a monopolar mode.
Figure 8:
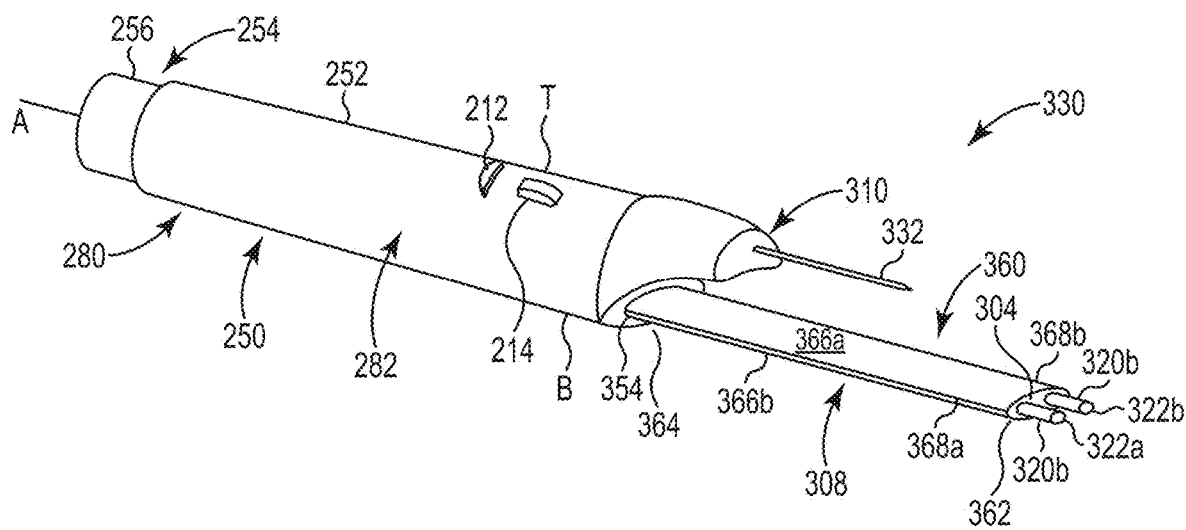
FIG. 8 is a perspective view of another example of the handheld electrosurgical device of FIG. 7 configured for use in a bipolar mode.

FIGS. 7 and 8 illustrate an exemplary multipurpose electrosurgical device 330 also constructed in accordance with the electrosurgical device 30 described above in FIG. 4. For example, the device 330 includes the cable input 80, switch mechanism 82, electrode tips 84, and interface 86 as described above.

Further, like parts with electrosurgical device 230 are labeled with like reference numerals. For example, electrosurgical device 330 can include the features of the handpiece 250 including the handle 252, proximal end 254, and strain relief 256. The proximal end 254 includes a cable input 280 configured to receive the distal end 88 of cable 24 and includes electrical connections 94, 96, 98 located within the handpiece 250 as well as fluid delivery tubing 16. The handle 252 can include a lower surface, or bottom B, and an upper surface, or top T. Additionally, the handpiece 250 includes a switch mechanism 282 to complete an electrical circuit between the conductors of cable input 280. In one example, the switch mechanism 282 includes push buttons 212 and 214 projecting from the upper surface or top T of the handle 252. Push buttons 212, 214 comprise hand switch assemblies for forming a closed circuit that can be sensed by an electrosurgical unit to selectively provide at least three variations of monopolar power and bipolar power as described above.

Rather than interchangeable electrode tips, however, the electrosurgical device 330 includes a retractable, or extendable, bipolar electrode shaft 308. The handpiece 250 of device 330 includes a distal end 352 with a monopolar electrode tip 310 and an opening 354. The monopolar electrode tip 310 in the example is fixed with respect to the handpiece 250, and the bipolar electrode shaft 308 is axially moveable with respect to the handpiece 250 through the opening 354. The monopolar electrode tip 310 includes blade 332 that may be shaped to form a sharp or razor-like blade. The bipolar electrode shaft 308 can be moved with respect to the handpiece 250 via a mechanism such as an attached thumb lever, not shown, and the handpiece/shaft combination can include a mechanism to releasably lock the bipolar electrode shaft 308 in the retracted and extended positions.

The bipolar electrode shaft 308 comprises a body 360 having first and second ends 362, 364, respectively and laterally opposed side surfaces 366a, 366b, joined by lateral edges 368a, 368b that may include rounded or chamfered edges configured so as to minimize or avoid inadvertent damage to tissue. In the example, sides 366a, 366b comprise substantially flat or planar surfaces. First end 362 includes a distal face that may include a fluid outlet port 304 in fluid communication with an internal lumen that is in fluid communication with delivery tubing 16. Alternatively, the sides 366a, 366b and/or edges 368a, 368b can include or also include fluid outlet ports for dispersing fluid.

Electrode tips 320a, 320b extend from the body portion 360 and, in the example, include blunt, rounded tips having distal-most electrode ends 322a, 322b, respectively. Distal-most electrode ends 322a, 322b may provide smooth continuous surfaces and in one example are devoid of points or edges. Electrode tips 320a, 320b may be configured to optimize tissue sealing or coagulation in conjunction with delivery of fluid 12 or for a particular application or anatomical geometry.

FIG. 7 illustrates the device 330 configured in a monopolar mode with the bipolar electrode shaft 322 retracted into the handpiece and the monopolar electrode blade 332 extends distally from the device 330. In the monopolar configuration, the monopolar electrode blade 332 is electrically coupled through the interface (disposed within the device 330 in this example), corresponding with interface 86, with the switching mechanism having components located within the device 330 and the electrosurgical unit. In monopolar mode, pressing pushbutton 212 provides monopolar RF energy corresponding with the cut function to the blade tip 332. Also, when the device 330 is configured in monopolar mode, pressing the other pushbutton 214 provides monopolar RF energy corresponding with the coagulation function to the blade tip 232. The bipolar electrodes ends 322a, 322b are deactivated in the monopolar configuration.

In the example device 330, bipolar electrode ends 322a, 322b are retracted within the handpiece 250 while in monopolar mode configuration. Other configurations are possible, and the electrode ends 322a, 322b can remain partially extended from handpiece 250 but disposed away, such as proximally, from the monopolar blade 332.

FIG. 8 illustrates the device 330 configured in a bipolar mode with the bipolar electrode shaft 322 protracted from the handpiece 250 to extend distally past the monopolar electrode blade 234. In the bipolar configuration, the monopolar electrode blade 334 is deactivated and one or both of pushbuttons 212, 214 can be depressed to activate the bipolar electrodes and dispense fluid 12 from the fluid port 304.

Electrodes and electrically conductive paths and contacts in electrosurgical devices 230, 330, can be formed from electrically conductive material such as metal and may comprise stainless steel, titanium, gold, silver, platinum or any other suitable material. Electrical pathways within the devices 230, 330 can be formed as wires, traces, or other pathways.

Other configurations of device 330 are contemplated, such as a device having bipolar electrode ends being fixed with respect to the handpiece 250 with the monopolar blade on a retractable/extendable shaft.

FIGS. 9-18 illustrate electrical schematics of examples of electrosurgical device 30. In particular, FIGS. 9-14 illustrate electrical schematics of examples of electrosurgical device 430a, 430b, 430c, 430d, 430e, 430f corresponding with the electrosurgical device 230 having interchangeable electrode tips. Also, FIGS. 15-18 illustrate electrical schematics of examples of electrosurgical device 530a, 530b corresponding with electrosurgical device 330 having retractable bipolar electrodes. These examples illustrate electrosurgical devices including a first conductor coupled to an energy detection system, such as switch input 94, a second conductor coupled to a source of RF energy, such as active input 96. The second conductor is operably configured to be coupled to an active electrode, such as bipolar electrode 122 or monopolar electrode 124 via a switch mechanism, such as switch mechanism 82. The monopolar electrode is activated at a first monopolar RF energy level when the switch mechanism is used to electrically couple the first and second conductors via a first circuit element. Also, the monopolar electrode is activated at a second monopolar RF energy level when the switch mechanism is used to electrically couple the first and second conductors via a second circuit element. Further, the bipolar electrode is activated at a bipolar RF energy level when the switch mechanism is used to electrically couple the first and second conductors in a bipolar mode.

The electrosurgical device 30 uses the circuit elements to cooperate with the electrosurgical unit 10 to detect the selected mode, i.e., either bipolar or monopolar, and the selected function, i.e., either cut or coagulation, within the monopolar mode. In one example, the electrosurgical unit includes a ladder topology to detect which switch has been closed, or button has been depressed, on the electrosurgical unit 30. The electrosurgical unit in this example uses three different impedances to determine the mode and function selected. In one example, the electrosurgical unit uses a generally 0 ohm resistance to indicate the device 30 is configured in a bipolar mode for hemostatic sealing and fluid delivery, a generally 69.8 ohm resistance to indicate the device 30 is in a monopolar mode at a first function, such as a coagulation function, and a generally 200 ohm resistance to indicate the device 30 is in a monopolar mode at a second function, such as a cut function. Other resistance values or circuit elements can be used, and the examples below are shown for illustration.

FIGS. 9-14 include example electrosurgical devices 430*a*, 430*b*, 430*c*, 430*d*, 430*e*, 430*f* respectively. Each of electrosurgical devices 430*a*, 430*b*, 430*c*, 430*d*, 430*e*, 430*f* include switch input 494, an active input 496, and a return input 498, which generally correspond with inputs 94, 96, 98, respectively, of device 30. Example devices 430*a*, 430*b*, 430*c*, 430*d*, 430*e*, 430*f* also include switch mechanisms 482*a*, 482*b*, 482*c*, 482*d*, 482*e*, 482*f* respectively, each having two switches, i.e. cut switch 412 and coagulation switch 414, coupled in parallel with switch input 494. Example devices 430*a*, 430*b*, 430*c*, 430*d* also include interface 486*a*, 486*b*, 486*c*, 486*d*, 486*e*, 486*f* respectively, each including four interface connections, i.e. cut switch connection 462, coagulation switch connection 464, active connection 466, and return connection 468. Further, each of example devices 430*a*, 430*b*, 430*c*, 430*d*, 430*e*, 430*f* include a first circuit element 436, such as a 200 ohm cut resistor, and a second circuit element 438, such as a 69.8 ohm coagulation resistor for use in a monopolar mode.

Figure 9:
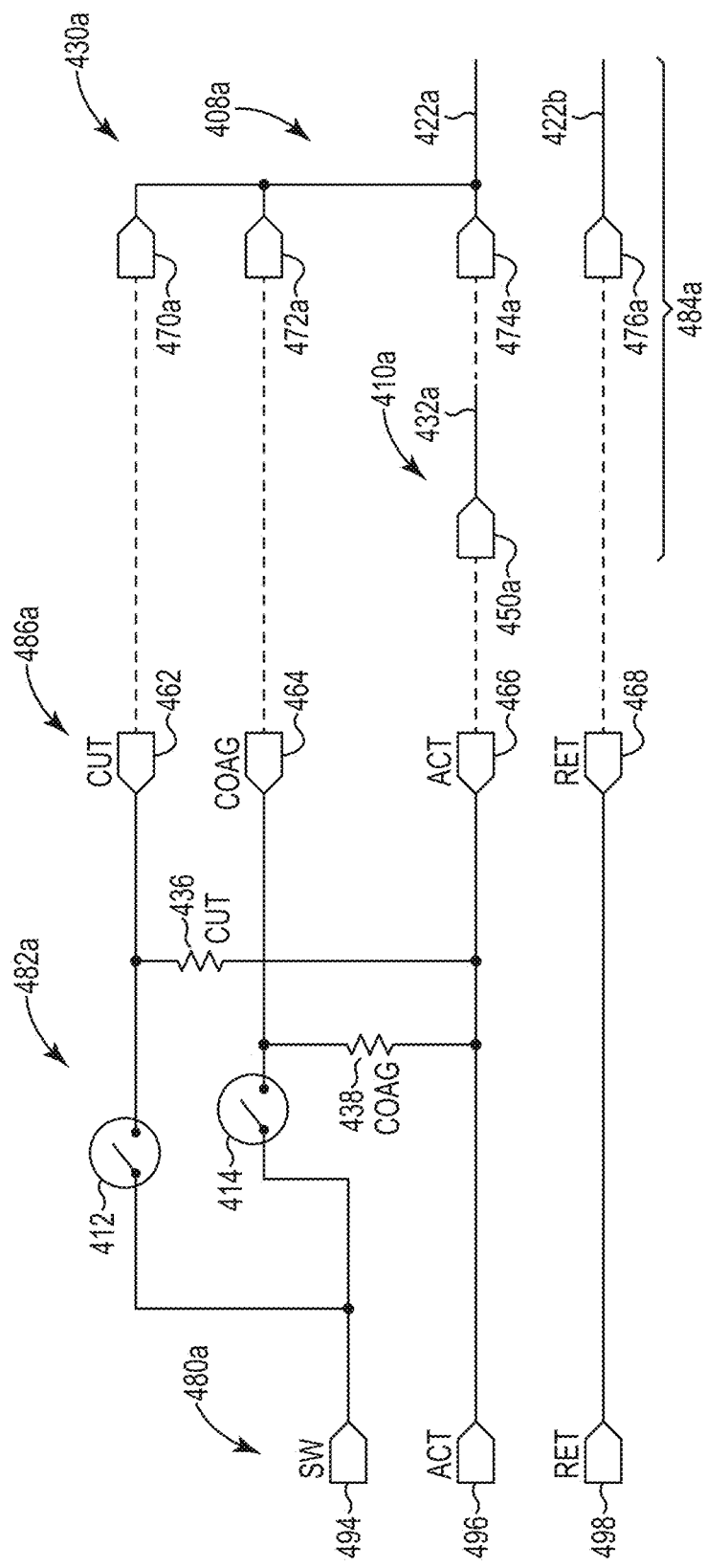
FIG. 9 is a schematic view of a circuit diagram of a handheld electrosurgical device of FIG. 4 including the bipolar and monopolar electrode tips of the electrosurgical device of FIG. 5 in a first example.

FIG. 9 illustrates example device 430*a* having inputs 480*a*, switch mechanism 482*a*, interface 486*a*, and electrode tips 484*a* configured to work with switch mechanism 482*a*. Switch mechanism 482*a* includes a cut switch 412 and cut resistor 436 coupled in series between the switch input 494 and active input 496. In the example illustrated, the cut switch connection 462 is electrically coupled between the cut switch 412 and the cut resistor 436. Switch mechanism 482*a* also includes a coagulation switch 414 and coagulation resistor 438 coupled in series between the switch input 494 and the active input 496. In the example illustrated, the coagulation switch connection 464 is electrically coupled between the coagulation switch 414 and the coagulation resistor 438. Also, the active input 496 is directly coupled to the active connection 466, and the return input 498 is directly coupled to the return connection 468.

Example device 430*a* further includes a monopolar electrode tip 410*a* configured to operate the device 430*a* in a monopolar mode. The monopolar electrode tip 410*a* includes a monopolar electrode blade tip 432*a* and a single electrical connection 450*a* configured to mate with the active connection 466. The monopolar electrode tip 410*a* does not include an electrical connection for the return connection 468. Additionally, the monopolar electrode tip 410*a* does not include an electrical connection for the cut connection 462 and the coagulation connection 464.

When the monopolar electrode tip 410*a* is coupled to the interface 486*a* as described, closing the cut switch 412 provides an electrical signal between the switch input 494 and the active input 496 through the cut resistor 436 to indicate to the electrosurgical unit 10 that the device 430*a* is to be operated in a cut function of the monopolar mode. Accordingly, the first RF energy level corresponding with a cut function is provided to the active input 496 and thus to the monopolar electrode blade tip 432*a* and returned through the tissue via a ground dispersive electrode (not shown).

When the monopolar electrode tip 410*a* is coupled to the interface 486*a* as described, closing the coagulation switch 414 provides an electrical signal between the switch input 494 and the active input 496 through the coagulation resistor 438 to indicate to the electrosurgical unit 10 that the device 430*a* is to be operated in a coagulation function of the monopolar mode. Accordingly, the second RF energy level corresponding with a coagulation function is provided to the active input 496 and thus to the monopolar electrode blade tip 432*a* and returned through the tissue via a ground dispersive electrode (not shown).

Example device 430*a* further includes a bipolar electrode tip 408*a* configured to operate the device 430*a* in a bipolar mode. The bipolar electrode tip 408*a* includes a active electrode tip 422*a* electrically coupled via conductors to three electrical connections 470*a*, 472*a*, 474*a* configured to mate with the cut connection 462, coagulation connection 464, and active connection 466, respectively. The bipolar electrode tip 408*a* further includes a return electrode end 422*b* electrically coupled via a conductor to a return connection 476*a* configured to mate with the return connection 468.

When the bipolar electrode tip 408*a* is coupled to the interface 486*a* as described, closing either the cut switch 412 or the coagulation switch 414 will provide an electrical signal directly between the switch input 494 and the active input 496, i.e., the connection will electrically short or include a resistance of about 0 ohms, to indicate to the electrosurgical unit 10 that the device 430*a* is to be operated in a bipolar mode. Accordingly, the third RF energy level corresponding with a bipolar mode is provided to the active input 496 and thus to the first electrode end 422*a* and returned through the tissue via the second electrode end 422*b*.

Electrosurgical device 430*a* can also be operated in bipolar mode with alternative electrode tips and, albeit with limited functionality.

For example, a bipolar electrode tip can includes an active electrode tip 422*a* electrically coupled via conductors to electrical connections configured to mate with coagulation connection 464 and active connection 466, instead of three electrical connections. The bipolar electrode tip further includes a return electrode end 422*b* electrically coupled via a conductor to a return connection configured to mate with the return connection 468. When the bipolar electrode tip is coupled to the interface as described, closing the coagulation switch 414 will provide an electrical signal directly between the switch input 494 and the active input 496, i.e., the connection will electrically short or include a resistance of about 0 ohms, to indicate to the electrosurgical unit 10 that the device 430*a* is to be operated in a bipolar mode. Accordingly, the third RF energy level corresponding with a bipolar mode is provided to the active input 496 and thus to the first electrode end 422*a* and returned through the tissue via the second electrode end 422*b*. The bipolar electrode tip will not be activated if the cut switch 412 is closed.

Another bipolar electrode tip of limited functionality includes an active electrode tip 422*a* electrically coupled via conductors to electrical connection configured to mate with cut connection 462 and active connection 466 instead of three electrical connections. The bipolar electrode tip further includes a return electrode end 422*b* electrically coupled via a conductor to a return connection configured to mate with the return connection 468. When the bipolar electrode tip is coupled to the interface 486*a* as described, closing the cut switch 412 will provide an electrical signal directly between the switch input 494 and the active input 496, i.e., the connection will electrically short or include a resistance of about 0 ohms, to indicate to the electrosurgical unit 10 that the device 430*a* is to be operated in a bipolar mode.

Accordingly, the third RF energy level corresponding with a bipolar mode is provided to the active input 496 and thus to the first electrode end 422a and returned through the tissue via the second electrode end 422b. The bipolar electrode tip 428a will not be activated if the coagulation switch 414 is closed.

Figure 10:
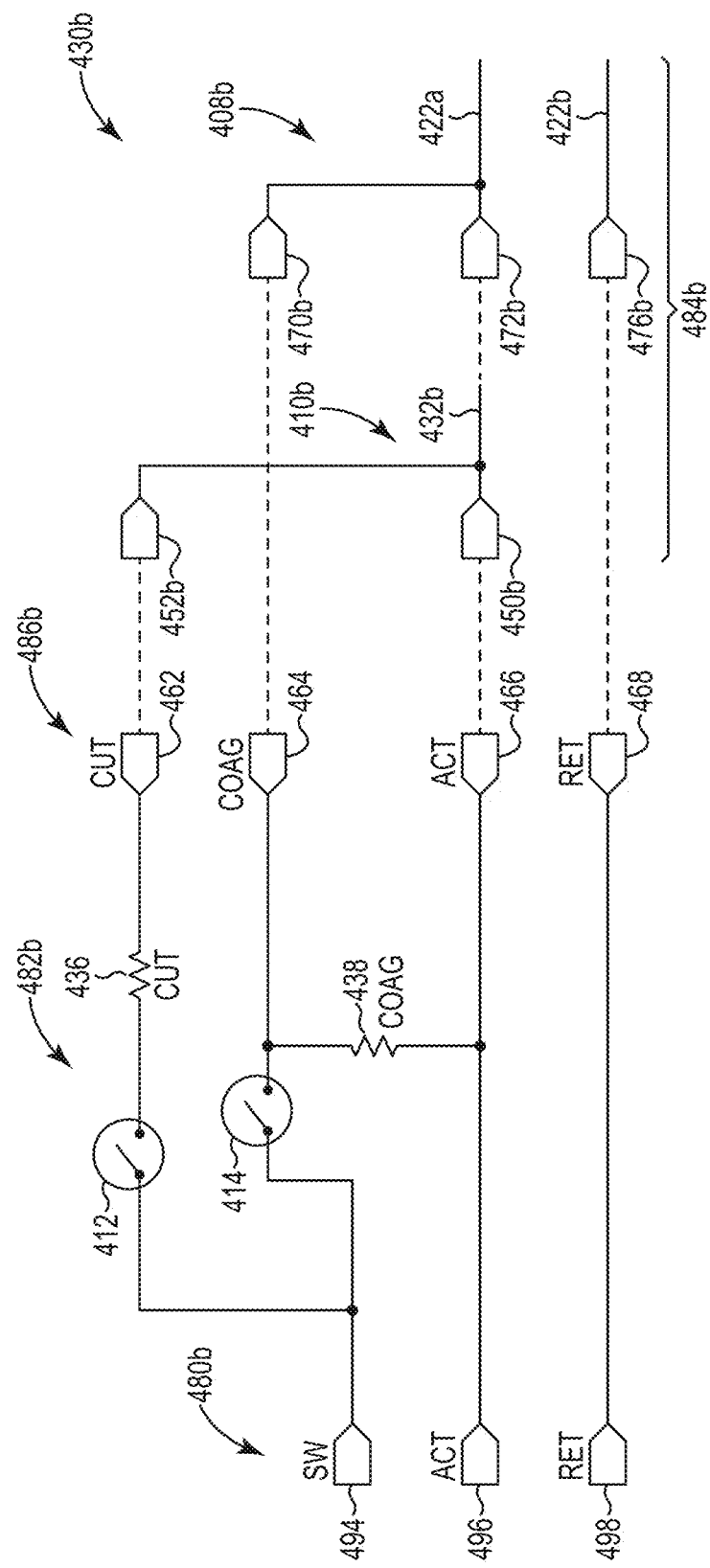
FIG. 10 is a schematic view of a circuit diagram of a handheld electrosurgical device of FIG. 4 including the bipolar and monopolar electrode tips of the electrosurgical device of FIG. 5 in a second example.

FIG. 10 illustrates example device 430b having inputs 480b, switch mechanism 482b, interface 486b, and electrode tips 484b configured to work with switch mechanism 482b. Switch mechanism 482b includes a cut switch 412 and cut resistor 436 coupled in series between the switch input 494 and cut switch connection 462. Switch mechanism 482b also includes a coagulation switch 414 and coagulation resistor 438 coupled in series between the switch input 494 and the active input 496. In the example illustrated, the coagulation switch connection 464 is electrically coupled between the coagulation switch 414 and the coagulation resistor 438. Also, the active input 496 is directly coupled to the active connection 466, and the return input 498 is directly coupled to the return connection 468.

Example device 430b further includes a monopolar electrode tip 410b configured to operate the device 430b in a monopolar mode. The monopolar electrode tip 410b includes a monopolar electrode blade tip 432b is electrically coupled to a first electrical connection 450b configured to mate with the active connection 466 and a second electrical connection 452b configured to mate with the cut connection 462. The monopolar electrode tip 410b does not include an electrical connection for the return connection 468. Additionally, the monopolar electrode tip 410b does not include an electrical connection for the coagulation connection 464.

When the monopolar electrode tip 410b is coupled to the interface 486b as described, closing the cut switch 412 provides an electrical signal between the switch input 494 and the active input 496 through the cut resistor 436 to indicate to the electrosurgical unit 10 that the device 430b is to be operated in a cut function of the monopolar mode. Accordingly, the first RF energy level corresponding with a cut function is provided to the active input 496 and thus to the monopolar electrode blade tip 432b and returned through the tissue via a ground dispersive electrode (not shown).

When the monopolar electrode tip 410b is coupled to the interface 486b as described, closing the coagulation switch 414 provides an electrical signal between the switch input 494 and the active input 496 through the coagulation resistor 438 to indicate to the electrosurgical unit 10 that the device 430b is to be operated in a coagulation function of the monopolar mode. Accordingly, the second RF energy level corresponding with a coagulation function is provided to the active input 496 and thus to the monopolar electrode blade tip 432b and returned through the tissue via a ground dispersive electrode (not shown).

Example device 430b further includes a bipolar electrode tip 408b configured to operate the device 430b in a bipolar mode. The bipolar electrode tip 410b includes an active electrode tip 422a electrically coupled via conductors to two electrical connections 470b, 472b configured to mate with the coagulation connection 464 and active connection 466, respectively. The bipolar electrode tip 408b further includes a return electrode end 422b electrically coupled via a conductor to a return connection 476b configured to mate with the return connection 468.

When the bipolar electrode tip 408b is coupled to the interface 486b as described, closing the coagulation switch 414 will provide an electrical signal directly between the switch input and the active input, i.e., the connection will electrically short or include a resistance of about 0 ohms, to indicate to the electrosurgical unit 10 that the device 430b is to be operated in a bipolar mode. Accordingly, the third RF energy level corresponding with a bipolar mode is provided to the active input and thus to the first electrode end 422a and returned through the tissue via the second electrode end 422b. In the example of bipolar electrode tip 408b, closing the cut switch 412 will not active the device 430b.

Figure 11:
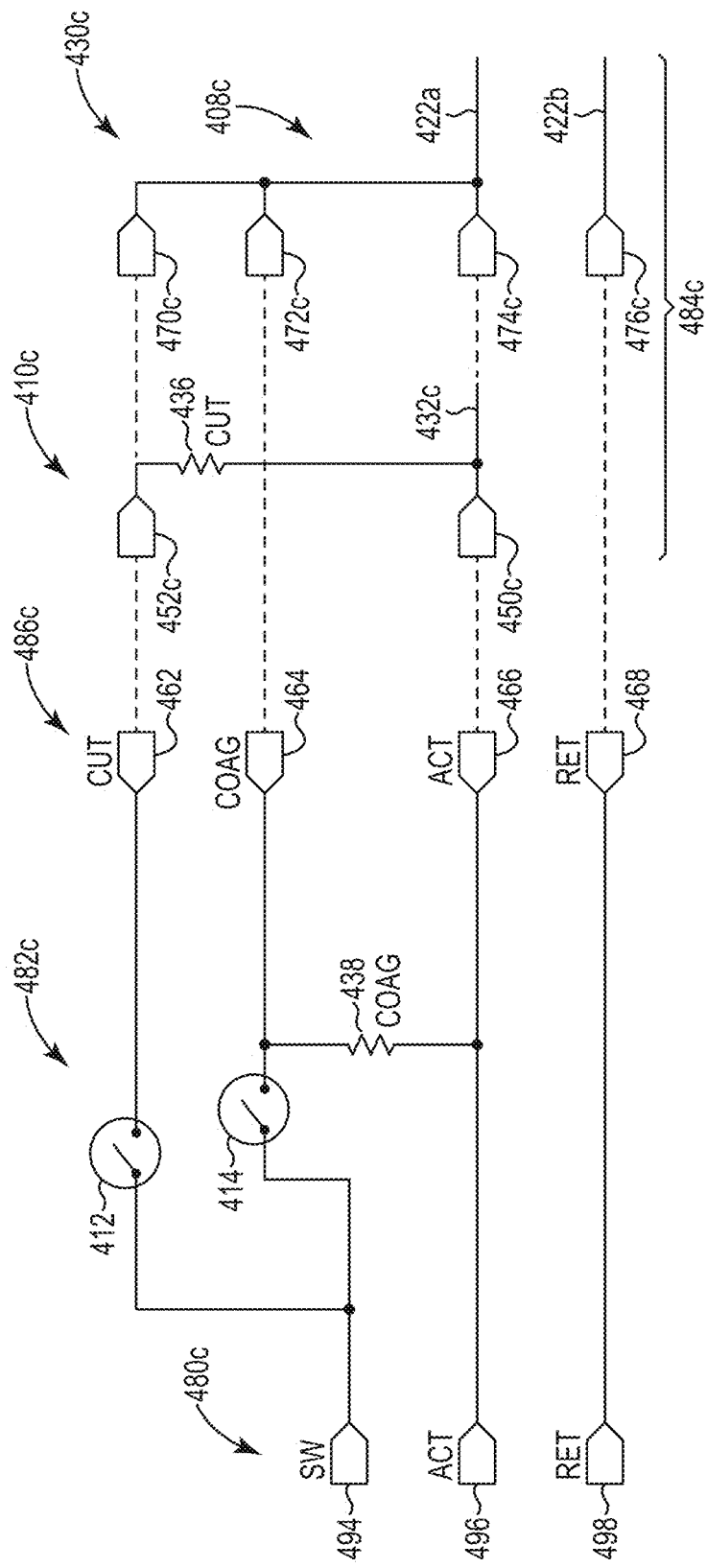
FIG. 11 is a schematic view of a circuit diagram of a handheld electrosurgical device of FIG. 4 including the bipolar and monopolar electrode tips of the electrosurgical device of FIG. 5 in a third example.

FIG. 11 illustrates example device 430c having inputs 480c, switch mechanism 482c, interface 486c, and electrode tips 484c configured to work with switch mechanism 482c. Switch mechanism 482c includes a cut switch 412 coupled in series between the switch input 494 and cut switch connection 462. Switch mechanism 482c also includes a coagulation switch 414 and coagulation resistor 438 coupled in series between the switch input 494 and the active input 496. In the example illustrated, the coagulation switch connection 464 is electrically coupled between the coagulation switch 414 and the coagulation resistor 438. Also, the active input 496 is directly coupled to the active connection 466, and the return input 498 is directly coupled to the return connection 468.

Example device 430c further includes a monopolar electrode tip 410c configured to operate the device 430c in a monopolar mode. The monopolar electrode tip 410c includes a monopolar electrode blade tip 432c is electrically coupled to a first electrical connection 450c configured to mate with the active connection 466 and a second electrical connection 452c configured to mate with the cut connection 462 via a cut resistor 436. The monopolar electrode tip 410c does not include an electrical connection for the return connection 468. Additionally, the monopolar electrode tip 410c does not include an electrical connection for the coagulation connection 464. In one example, the cut resistor 436 can be disposed within the monopolar body portion 210a of FIG. 5.

When the monopolar electrode tip 410c is coupled to the interface 486c as described, closing the cut switch 412 provides an electrical signal between the switch input 494 and the active input 496 through the cut resistor 436 in the electrode tip 410c to indicate to the electrosurgical unit 10 that the device 430c is to be operated in a cut function of the monopolar mode. Accordingly, the first RF energy level corresponding with a cut function is provided to the active input 496 and thus to the monopolar electrode blade tip 432c and returned through the tissue via a ground dispersive electrode (not shown).

When the monopolar electrode tip 410c is coupled to the interface 486c as described, closing the coagulation switch 414 provides an electrical signal between the switch input 494 and the active input 496 through the coagulation resistor 438 in the switch mechanism 482c to indicate to the electrosurgical unit 10 that the device 430c is to be operated in a coagulation function of the monopolar mode. Accordingly, the second RF energy level corresponding with a coagulation function is provided to the active input 496 and thus to the monopolar electrode blade tip 432c and returned through the tissue via a ground dispersive electrode (not shown).

Example device 430c further includes a bipolar electrode tip 408c configured to operate the device 430c in a bipolar mode. The bipolar electrode tip 410c includes a active electrode tip 422a electrically coupled via conductors to three electrical connections 470c, 472c, 474c configured to mate with the cut connection 462, coagulation connection 464, and active connection 466, respectively. The bipolar electrode tip 408c further includes a return electrode end 422b electrically coupled via a conductor to a return connection 476c configured to mate with the return connection 468.

When the bipolar electrode tip 408c is coupled to the interface 486c as described, closing either the cut switch 412 or the coagulation switch 414 will provide an electrical signal directly between the switch input 494 and the active input 496, i.e., the connection will electrically short or include a resistance of about 0 ohms, to indicate to the electrosurgical unit 10 that the device 430c is to be operated in a bipolar mode. Accordingly, the third RF energy level corresponding with a bipolar mode is provided to the active input 496 and thus to the first electrode end 422a and returned through the tissue via the second electrode end 422b.

Electrosurgical device 430c can also be operated in bipolar mode with alternative electrode tips, albeit with limited functionality.

One such bipolar electrode tip includes an active electrode tip 422a electrically coupled via conductors to electrical connections configured to mate with coagulation connection 464 and active connection 466. The bipolar electrode tip further includes a return electrode end 422b electrically coupled via a conductor to a return connection configured to mate with the return connection 468. When the bipolar electrode tip is coupled to the interface 486c as described, closing the coagulation switch 414 will provide an electrical signal directly between the switch input 494 and the active input 496, i.e., the connection will electrically short or include a resistance of about 0 ohms, to indicate to the electrosurgical unit 10 that the device 430c is to be operated in a bipolar mode. Accordingly, the third RF energy level corresponding with a bipolar mode is provided to the active input and thus to the first electrode end 422a and returned through the tissue via the second electrode end 422b. The bipolar electrode tip 418c will not be activated if the cut switch 412 is closed.

Another such bipolar electrode tip with limited functionality includes an active electrode tip 422a electrically coupled via conductors to electrical connection configured to mate with cut connection 462 and active connection 466. The bipolar electrode tip further includes a return electrode end 422b electrically coupled via a conductor to a return connection configured to mate with the return connection 468. When the bipolar electrode tip is coupled to the interface 486c as described, closing the cut switch 412 will provide an electrical signal directly between the switch input 494 and the active input 496, i.e., the connection will electrically short or include a resistance of about 0 ohms, to indicate to the electrosurgical unit 10 that the device 430c is to be operated in a bipolar mode. Accordingly, the third RF energy level corresponding with a bipolar mode is provided to the active input and thus to the first electrode end 422a and returned through the tissue via the second electrode end 422b. The bipolar electrode tip 428c will not be activated if the coagulation switch 414 is closed.

Figure 12:
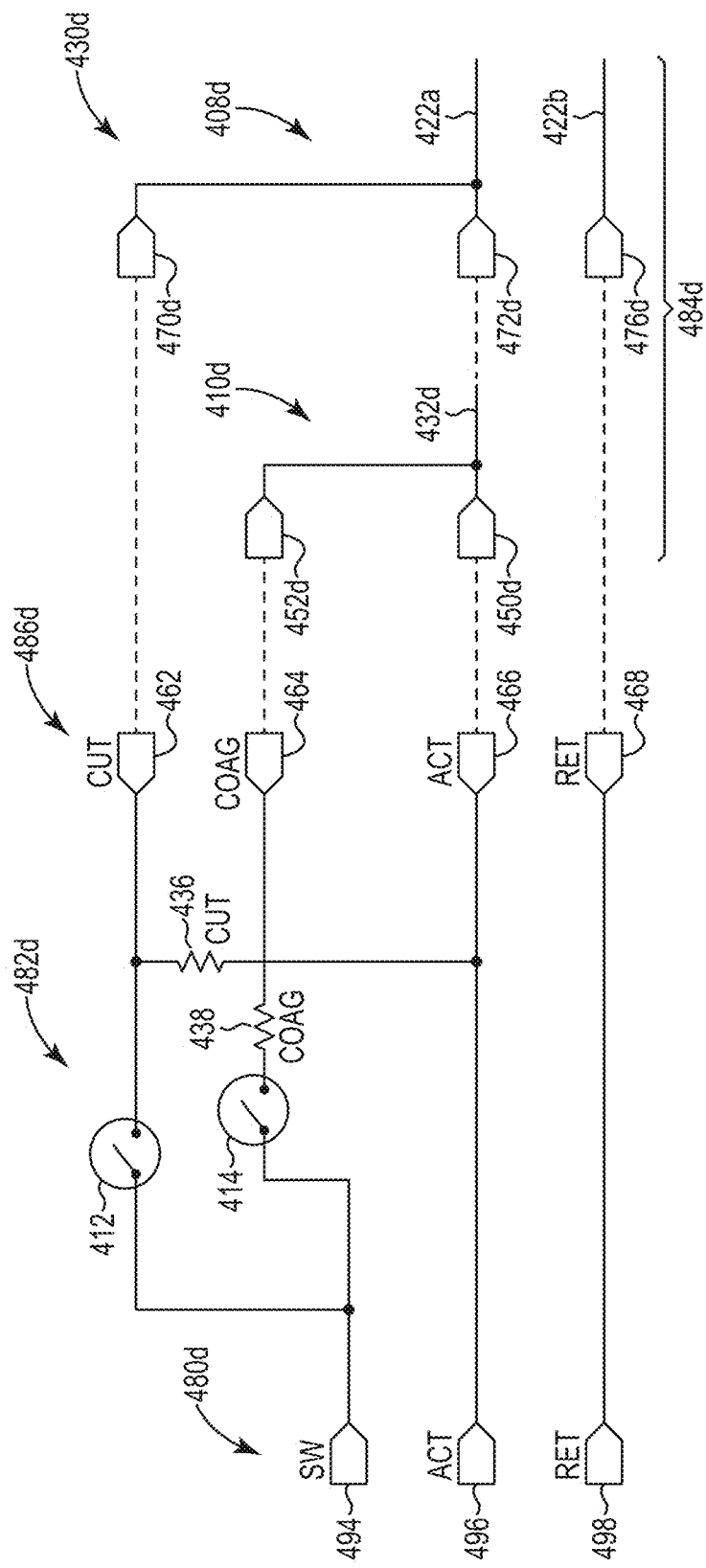
FIG. 12 is a schematic view of a circuit diagram of a handheld electrosurgical device of FIG. 4 including the bipolar and monopolar electrode tips of the electrosurgical device of FIG. 5 in a fourth example.

FIG. 12 illustrates example device 430d having inputs 480d, switch mechanism 482d, interface 486d, and electrode tips 484d configured to work with switch mechanism 482d. Switch mechanism 482d includes a cut switch 412 and cut resistor 436 coupled in series between the switch input 494 and the active input 496. In the example, illustrated, the cut switch connection 462 is electrically coupled between the cut switch 412 and the cut resistor 436. Switch mechanism 482d also includes a coagulation switch 414 and coagulation resistor 438 coupled in series between the switch input 494 and the coagulation switch connection 464. Also, the active input 496 is directly coupled to the active connection 466, and the return input 498 is directly coupled to the return connection 468.

Example device 430d further includes a monopolar electrode tip 410d configured to operate the device 430d in a monopolar mode. The monopolar electrode tip 410d includes a monopolar electrode blade tip 432d is electrically coupled to a first electrical connection 450d configured to mate with the active connection 466 and a second electrical connection 452d configured to mate with the coagulation connection 464. The monopolar electrode tip 410c does not include an electrical connection for the return connection 468. Additionally, the monopolar electrode tip 410d does not include an electrical connection for the cut connection 462.

When the monopolar electrode tip 410d is coupled to the interface 486d as described, closing the cut switch 412 provides an electrical signal between the switch input 494 and the active input 496 through the cut resistor 436 to indicate to the electrosurgical unit 10 that the device 430d is to be operated in a cut function of the monopolar mode. Accordingly, the first RF energy level corresponding with a cut function is provided to the active input 496 and thus to the monopolar electrode blade tip 432d and returned through the tissue via a ground dispersive electrode (not shown).

When the monopolar electrode tip 410d is coupled to the interface 486d as described, closing the coagulation switch 414 provides an electrical signal between the switch input 494 and the active input 496 through the coagulation resistor 438 to indicate to the electrosurgical unit 10 that the device 430d is to be operated in a coagulation function of the monopolar mode. Accordingly, the second RF energy level corresponding with a coagulation function is provided to the active input 496 and thus to the monopolar electrode blade tip 432d and returned through the tissue via a ground dispersive electrode (not shown).

Example device 430d further includes a bipolar electrode tip 408d configured to operate the device 430d in a bipolar mode. The bipolar electrode tip 410d includes a active electrode tip 422a electrically coupled via conductors to two electrical connections 470d, 472d configured to mate with the cut connection 462 and active connection 466, respectively. The bipolar electrode tip 408d further includes a return electrode end 422b electrically coupled via a conductor to a return connection 476d configured to mate with the return connection 468.

When the bipolar electrode tip 408d is coupled to the interface 486d as described, closing the coagulation switch 414 will provide an electrical signal directly between the switch input 494 and the active input 496, i.e., the connection will electrically short or include a resistance of about 0 ohms, to indicate to the electrosurgical unit 10 that the device 430d is to be operated in a bipolar mode. Accordingly, the third RF energy level corresponding with a bipolar mode is provided to the active input 496 and thus to the first electrode end 422a and returned through the tissue via the second electrode end 422b. In the example of bipolar electrode tip 408d, closing the coagulation switch 414 will not activate the device 430d.

Figure 13:
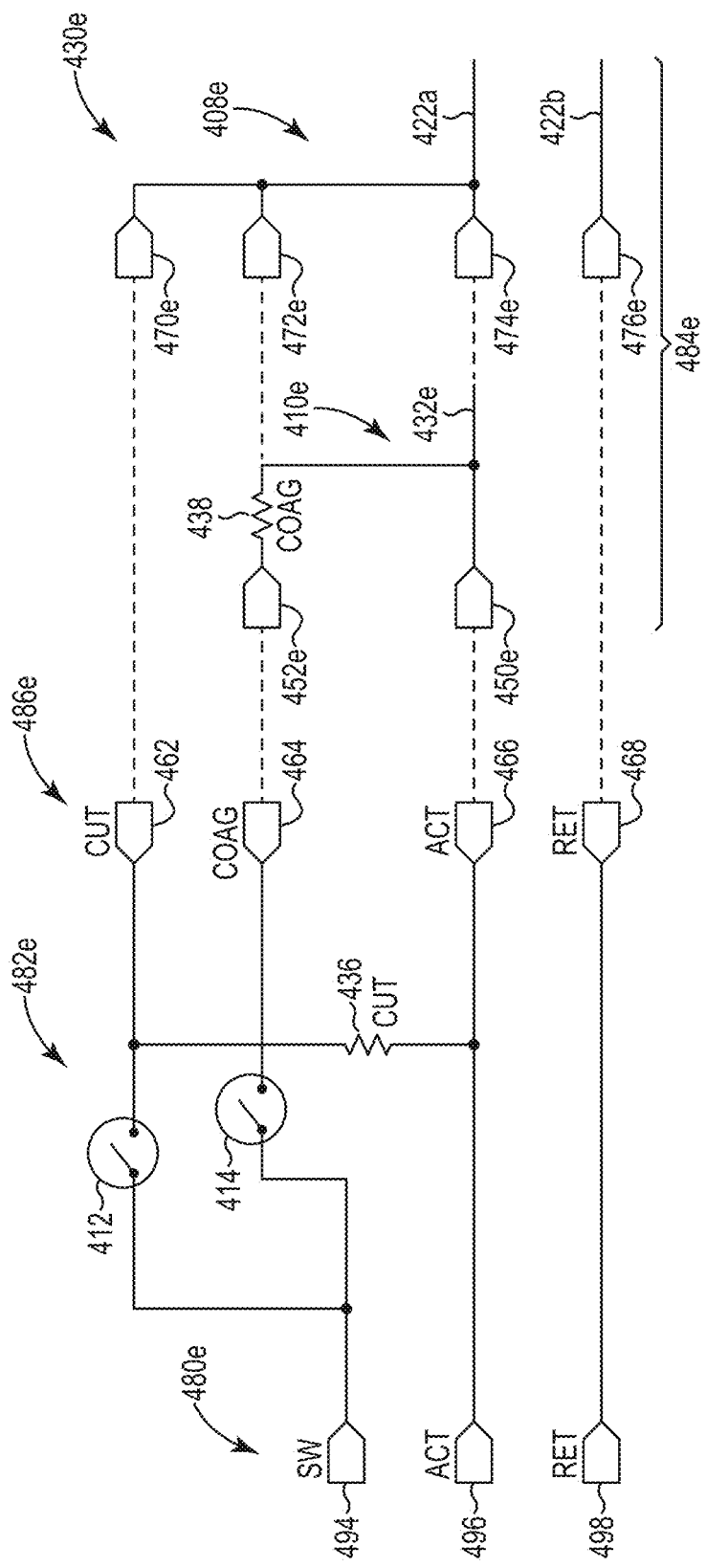
FIG. 13 is a schematic view of a circuit diagram of a handheld electrosurgical device of FIG. 4 including the bipolar and monopolar electrode tips of the electrosurgical device of FIG. 5 in a fifth example.

FIG. 13 illustrates example device 430e having inputs 480e, switch mechanism 482e, interface 486e, and electrode tips 484e configured to work with switch mechanism 482e. Switch mechanism 482e includes a coagulation switch 414 coupled in series between the switch input 494 and coagulation switch connection 464. Switch mechanism 482e also includes a cut switch 412 and cut resistor 436 coupled in series between the switch input 494 and the active input 496. In the example illustrated, the cut switch connection 462 is electrically coupled between the cut switch 412 and the cut resistor 436. Also, the active input 496 is directly coupled to the active connection 466, and the return input 498 is directly coupled to the return connection 468.

Example device 430e further includes a monopolar electrode tip 410e configured to operate the device 430e in a monopolar mode. The monopolar electrode tip 410e includes a monopolar electrode blade tip 432e is electrically coupled to a first electrical connection 450e configured to mate with the active connection 466 and a second electrical connection 452e configured to mate with the coagulation connection 464 via a coagulation resistor 438. The monopolar electrode tip 410e does not include an electrical connection for the return connection 468. Additionally, the monopolar electrode tip 410e does not include an electrical connection for the cut connection 462. In one example, the coagulation resistor 438 can be disposed within the monopolar body portion 210a of FIG. 5.

When the monopolar electrode tip 410e is coupled to the interface 486e as described, closing the cut switch 412 provides an electrical signal between the switch input 494 and the active input 496 through the cut resistor 436 in the switch mechanism 482e to indicate to the electrosurgical unit 10 that the device 430e is to be operated in a cut function of the monopolar mode. Accordingly, the first RF energy level corresponding with a cut function is provided to the active input 496 and thus to the monopolar electrode blade tip 432e and returned through the tissue via a ground dispersive electrode (not shown).

When the monopolar electrode tip 410e is coupled to the interface 486e as described, closing the coagulation switch 414 provides an electrical signal between the coagulation switch input 494 and the active input 496 through the coagulation resistor 438 in the electrode tip 484e to indicate to the electrosurgical unit 10 that the device 430e is to be operated in a coagulation function of the monopolar mode. Accordingly, the second RF energy level corresponding with a coagulation function is provided to the active input 496 and thus to the monopolar electrode blade tip 432e and returned through the tissue via a ground dispersive electrode (not shown).

Example device 430e further includes a bipolar electrode tip 408e configured to operate the device 430e in a bipolar mode. The bipolar electrode tip 410e includes a active electrode tip 422a electrically coupled via conductors to three electrical connections 470e, 472e, 474e configured to mate with the cut connection 462, coagulation connection 464, and active connection 466, respectively. The bipolar electrode tip 408e further includes a return electrode end 422b electrically coupled via a conductor to a return connection 476e configured to mate with the return connection 468.

When the bipolar electrode tip 408e is coupled to the interface 486e as described, closing either the cut switch 412 or the coagulation switch 414 will provide an electrical signal directly between the switch input 494 and the active input 496, i.e., the connection will electrically short or include a resistance of about 0 ohms, to indicate to the electrosurgical unit 10 that the device 430e is to be operated in a bipolar mode. Accordingly, the third RF energy level corresponding with a bipolar mode is provided to the active input 496 and thus to the first electrode end 422a and returned through the tissue via the second electrode end 422b.

Electrosurgical device 430e can also be operated in bipolar mode with alternative electrode tips, albeit with limited functionality.

One such bipolar electrode tip includes an active electrode tip 422a electrically coupled via conductors to electrical connections configured to mate with coagulation connection 464 and active connection 466. The bipolar electrode tip further includes a return electrode end 422b electrically coupled via a conductor to a return connection configured to mate with the return connection 468. When the bipolar electrode tip is coupled to the interface 486e as described, closing the coagulation switch 414 will provide an electrical signal directly between the switch input 494 and the active input 496, i.e., the connection will electrically short or include a resistance of about 0 ohms, to indicate to the electrosurgical unit 10 that the device 430e is to be operated in a bipolar mode. Accordingly, the third RF energy level corresponding with a bipolar mode is provided to the active input and thus to the first electrode end 422a and returned through the tissue via the second electrode end 422b. The bipolar electrode tip 418e will not be activated if the cut switch 412 is closed.

Another such limited functionality bipolar electrode tip includes an active electrode tip 422a electrically coupled via conductors to electrical connections configured to mate with cut connection 462 and active connection 466. The bipolar electrode tip further includes a return electrode end 422b electrically coupled via a conductor to a return connection configured to mate with the return connection 468. When the bipolar electrode tip 428e is coupled to the interface 486e as described, closing the cut switch 412 will provide an electrical signal directly between the switch input 494 and the active input 496, i.e., the connection will electrically short or include a resistance of about 0 ohms, to indicate to the electrosurgical unit 10 that the device 430e is to be operated in a bipolar mode. Accordingly, the third RF energy level corresponding with a bipolar mode is provided to the active input and thus to the first electrode end 422a and returned through the tissue via the second electrode end 422b. The bipolar electrode tip will not be activated if the coagulation switch 414 is closed.

Figure 14:
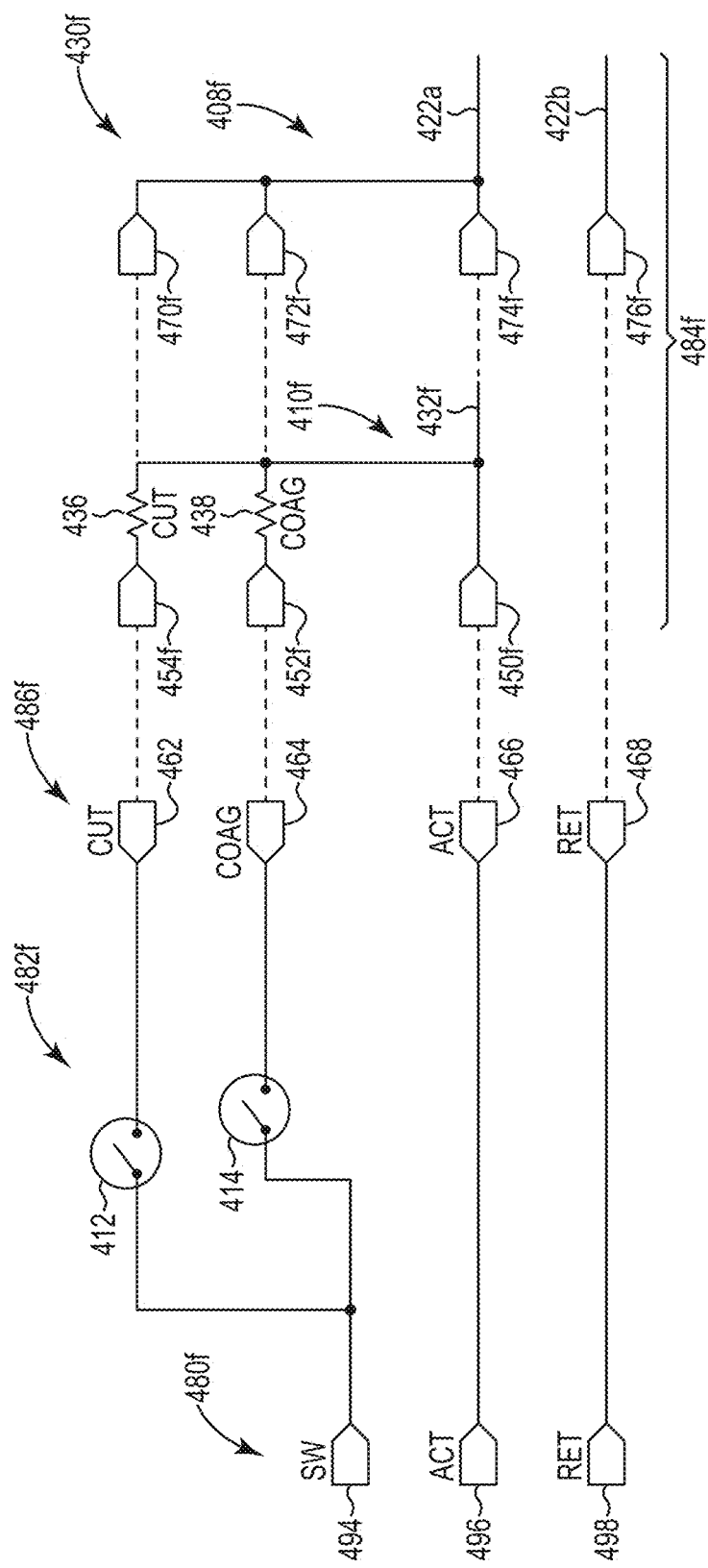
FIG. 14 is a schematic view of a circuit diagram of a handheld electrosurgical device of FIG. 4 including the bipolar and monopolar electrode tips of the electrosurgical device of FIG. 5 in a sixth example.

FIG. 14 illustrates example device 430f having inputs 480f, switch mechanism 482f, interface 486f, and electrode tips 484f configured to work with switch mechanism 482f. Switch mechanism 482f includes a cut switch 412 coupled in series between the switch input 494 and cut switch connection 462. Switch mechanism 482f also includes a coagulation switch 414 coupled in series between the switch input 494 and the coagulation switch connection 464. Also, the active input 496 is directly coupled to the active connection 466, and the return input 498 is directly coupled to the return connection 468.

Example device 430f further includes a monopolar electrode tip 410f configured to operate the device 430f in a monopolar mode. The monopolar electrode tip 410c includes a monopolar electrode blade tip 432c is electrically coupled to a first electrical connection 450c configured to mate with the active connection 466, a second electrical connection 452f (in parallel with the first electrical connection 450f) and configured to mate with the coagulation connection 464 via a coagulation resistor 438, and a third electrical connection 454f configured to mate with the cut connection 462 via a cut resistor 436 (in parallel with the first electrical connection 450f and the coagulation resistor 438). The monopolar electrode tip 410c does not include an electrical connection for the return connection 468. In one example, the cut resistor 436 and the coagulation resistor 438 can be disposed within the monopolar body portion 210a of FIG. 5.

When the monopolar electrode tip 410f is coupled to the interface 486f as described, closing the cut switch 412 provides an electrical signal between the switch input 494 and the active input 496 through the cut resistor 436 in the electrode tip 410f to indicate to the electrosurgical unit 10 that the device 430f is to be operated in a cut function of the monopolar mode. Accordingly, the first RF energy level corresponding with a cut function is provided to the active input 496 and thus to the monopolar electrode blade tip 432f and returned through the tissue via a ground dispersive electrode (not shown).

When the monopolar electrode tip 410f is coupled to the interface 486f as described, closing the coagulation switch 414 provides an electrical signal between the switch input 494 and the active input 496 through the coagulation resistor 438 in the electrode tip 410f to indicate to the electrosurgical unit 10 that the device 430f is to be operated in a coagulation function of the monopolar mode. Accordingly, the second RF energy level corresponding with a coagulation function is provided to the active input 496 and thus to the monopolar electrode blade tip 432f and returned through the tissue via a ground dispersive electrode (not shown).

Example device 430f further includes a bipolar electrode tip 408f configured to operate the device 430f in a bipolar mode. The bipolar electrode tip 410f includes a active electrode tip 422a electrically coupled via conductors to three electrical connections 470f, 472f, 474f configured to mate with the cut connection 462, coagulation connection 464, and active connection 466, respectively. The bipolar electrode tip 408f further includes a return electrode end 422b electrically coupled via a conductor to a return connection 476f configured to mate with the return connection 468.

When the bipolar electrode tip 408f is coupled to the interface 486f as described, closing either the cut switch 412 or the coagulation switch 414 will provide an electrical signal directly between the switch input 494 and the active input 496, i.e., the connection will electrically short or include a resistance of about 0 ohms, to indicate to the electrosurgical unit 10 that the device 430f is to be operated in a bipolar mode. Accordingly, the third RF energy level corresponding with a bipolar mode is provided to the active input 496 and thus to the first electrode end 422a and returned through the tissue via the second electrode end 422b.

Electrosurgical device 430f can also be operated in bipolar mode with alternative electrode tips 418c and 428f, albeit with limited functionality.

Bipolar electrode tip 418f includes an active electrode tip 422a electrically coupled via conductors to electrical connection 440f, 442f configured to mate with coagulation connection 464 and active connection 466, respectively. The bipolar electrode tip 418f further includes a return electrode end 422b electrically coupled via a conductor to a return connection 448f configured to mate with the return connection 468. When the bipolar electrode tip 418f is coupled to the interface 486f as described, closing the coagulation switch 414 will provide an electrical signal directly between the switch input 494 and the active input 496, i.e., the connection will electrically short or include a resistance of about 0 ohms, to indicate to the electrosurgical unit 10 that the device 430f is to be operated in a bipolar mode. Accordingly, the third RF energy level corresponding with a bipolar mode is provided to the active input and thus to the first electrode end 422a and returned through the tissue via the second electrode end 422b. The bipolar electrode tip 418f will not be activated if the cut switch 412 is closed.

Bipolar electrode tip 428f includes an active electrode tip 422a electrically coupled via conductors to electrical connection 444f, 446f configured to mate with cut connection 462 and active connection 466, respectively. The bipolar electrode tip 428f further includes a return electrode end 422b electrically coupled via a conductor to a return connection 448f configured to mate with the return connection 468. When the bipolar electrode tip 428f is coupled to the interface 486f as described, closing the cut switch 412 will provide an electrical signal directly between the switch input 494 and the active input 496, i.e., the connection will electrically short or include a resistance of about 0 ohms, to indicate to the electrosurgical unit 10 that the device 430f is to be operated in a bipolar mode. Accordingly, the third RF energy level corresponding with a bipolar mode is provided to the active input and thus to the first electrode end 422a and returned through the tissue via the second electrode end 422b. The bipolar electrode tip 428f will not be activated if the coagulation switch 414 is closed.

Other examples of the electrosurgical device 30 having interchangeable electrode tips are possible, and advantages of each may become apparent. For instance, the example of device 430c, with cut resistor 436 and coagulation resistor 438 (or other appropriate circuit elements) located within the switch mechanism 482a, may include the advantage of having electrode tips 484a that are easily manufactured. The example of device 430f, with circuit elements such as cut resistor 436 and coagulation resistor 438 in the monopolar tip 410f, may include the advantage of having a handpiece that can work with electrosurgical units that include different impedance values for detecting mode and function. Interchangeable electrode tips 484f can be configured to include circuit elements that correspond with the electrosurgical unit.

FIGS. 15-16 and FIGS. 17-18 illustrate include example electrosurgical devices 530a, 530b, respectively that include retractable bipolar shaft 508a, 508b, respectively and can correspond with electrosurgical device 330 of FIGS. 7-8. Each of electrosurgical devices 530a, 530b include switch input 594, an active input 596, and a return input 598, which generally correspond with inputs 94, 96, 98, respectively, of device 30. Example devices 530a, 530b also include switch mechanisms 582a, 582b respectively, each having two switches, i.e. cut switch 512 and coagulation switch 514, coupled in parallel with switch input 594. Example devices 530a, 530b also include interface 586a, 586b, respectively, each including five interface connections, i.e. monopolar active 560, cut switch connection 562, coagulation switch connection 564, active connection 566, return connection 568. Further, each of example devices 530a, 530b, include a first circuit element 536, such as a 200 ohm cut resistor, and a second circuit element 538, such as a 69.8 ohm coagulation resistor for use in a monopolar mode.

Example electrosurgical devices 530a, 530b include three inputs 594, 596, 598 that can correspond with inputs 494, 496, 498 of electrosurgical devices 430a, 430b, 430c, 430d, 430e, 430f described above. Additionally, electrosurgical devices 530a, 530b include switch mechanisms 582a, 582b that can correspond with switch mechanisms 482a, 482b, respectively, described above. One skilled in the art can now readily recognize that additional embodiments of electrosurgical device 330 can be constructed using the switch mechanisms 482c-48f of devices 430c-430f described above. Further, one skilled in the art can now readily recognize that additional embodiments of electrosurgical device 330 can be constructed including bipolar shaft 308 with possibly limited functionality of the buttons 212, 214 in bipolar mode.

Figure 15:
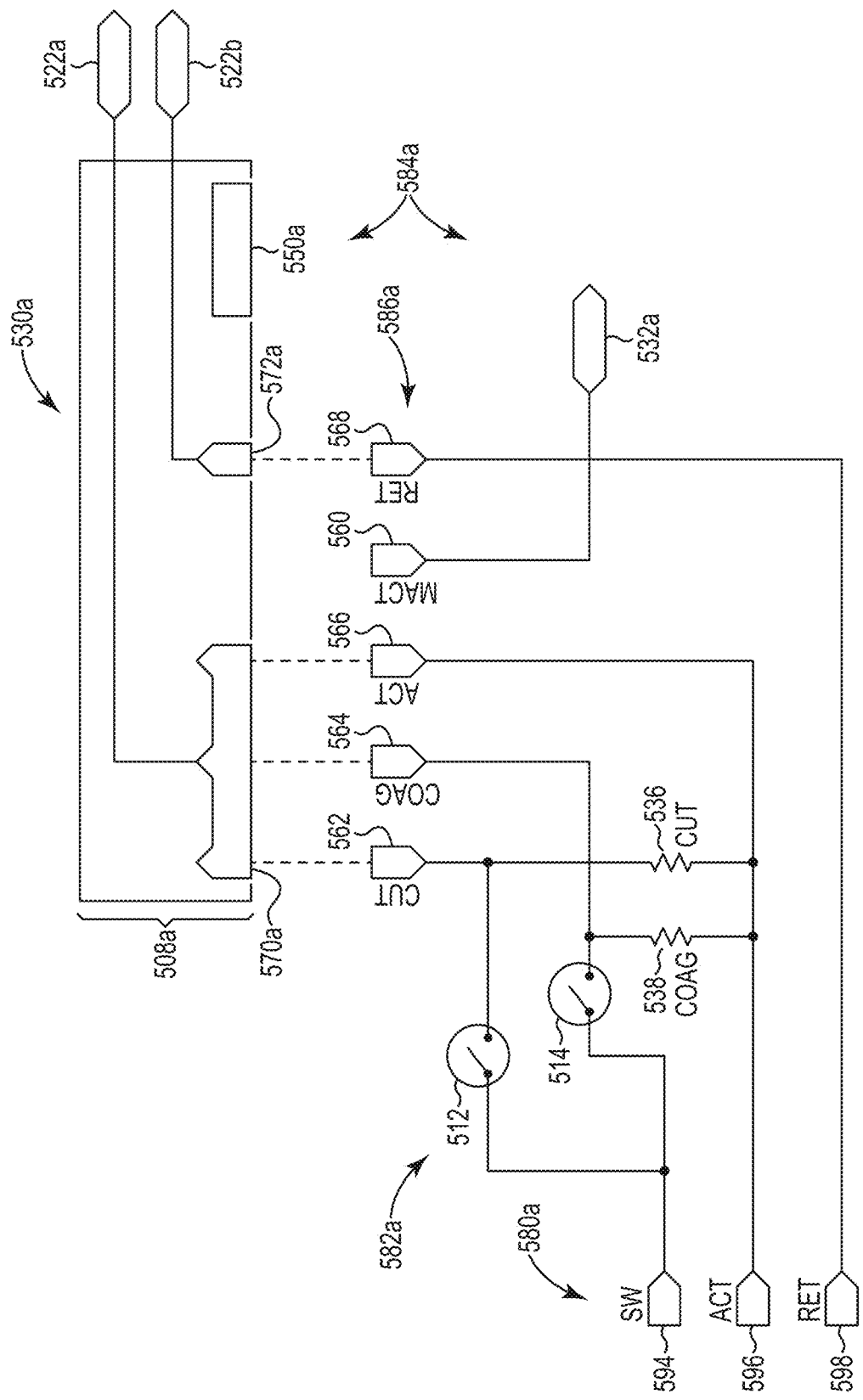
FIG. 15 is a schematic view of a circuit diagram of a handheld electrosurgical device of FIG. 4 configured as a first example the electrosurgical device of FIG. 8 in a bipolar mode.
Figure 16:
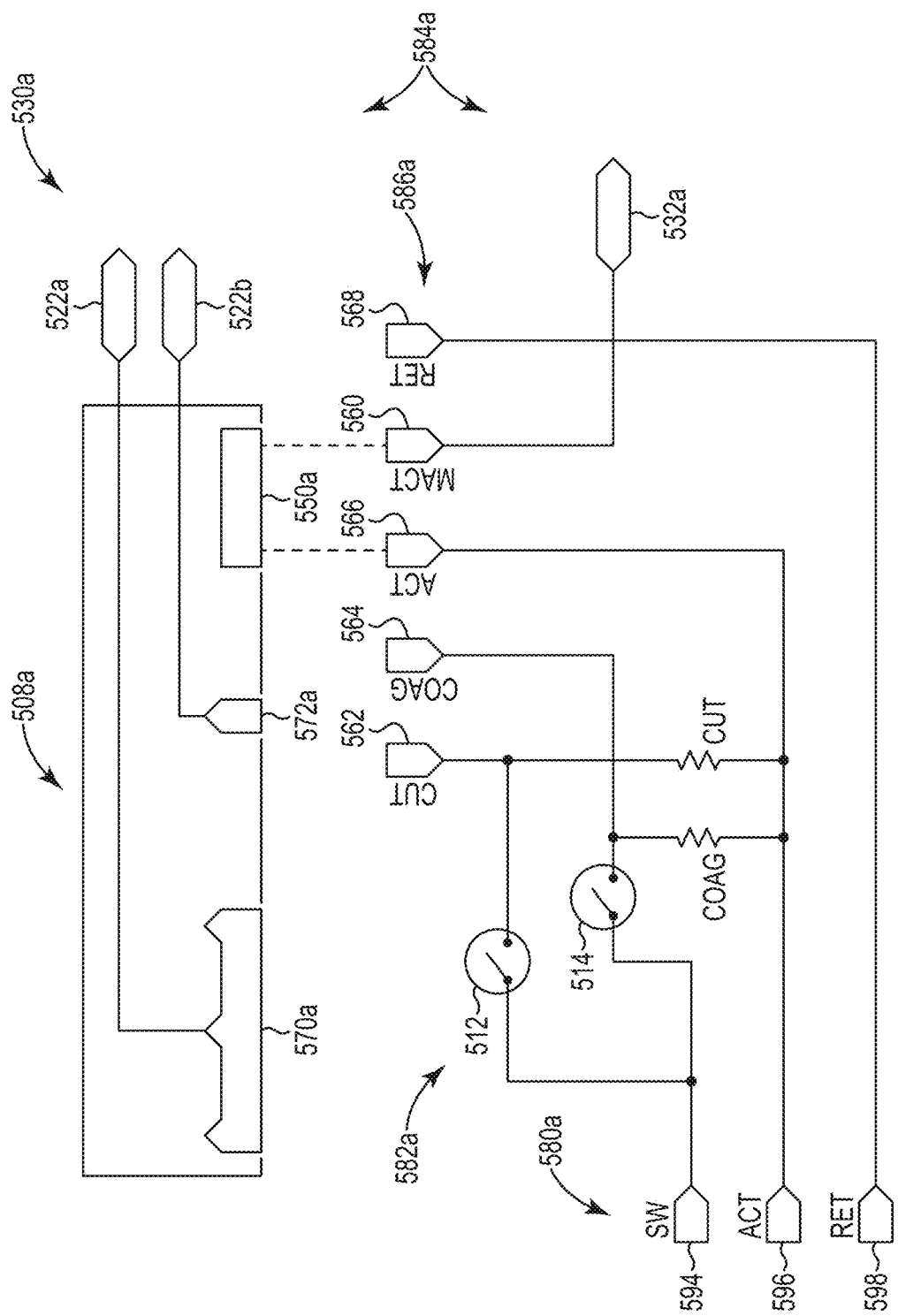
FIG. 16 is a schematic view of a circuit diagram of a handheld electrosurgical device of FIG. 4 configured as a first example the electrosurgical device of FIG. 7 in a monopolar mode.

FIGS. 15-16 illustrate example device 530a having inputs 580a, switch mechanism 582a, interface 586a, and electrode tips 584a configured to work with switch mechanism 582a. Switch mechanism 582a includes a cut switch 512 and cut resistor 536 coupled in series between the switch input 594 and active input 596. In the example illustrated, the cut switch connection 562 is electrically coupled between the cut switch 512 and the cut resistor 536. Switch mechanism 582a also includes a coagulation switch 514 and coagulation resistor 538 coupled in series between the switch input 594 and the active input 596. In the example illustrated, the coagulation switch connection 564 is electrically coupled between the coagulation switch 514 and the coagulation resistor 538. Also, the active input 596 is directly coupled to the active connection 566, and the return input 598 is directly coupled to the return connection 568.

Example device 530a further includes a monopolar electrode tip 510a configured to operate the device 530a in a monopolar mode. The monopolar electrode tip 510a includes a monopolar electrode blade 532a that is electrically coupled to monopolar active connection 560a.

Example device 530a further includes a bipolar shaft 508a that includes an active electrode end 522a and a return electrode end 522b extending from the shaft 508a at, for example, a first end 562a, that may correspond with first end 362 of device 330. The active electrode end 522a is electrically coupled via conductor to an active bipolar connection 570a, and the return electrode end 522b is electrically coupled via conductor to a return bipolar connection 572a. In the example, connections 570a, 572a are exposed on the surface of the shaft 508a proximate the second end 564a that may correspond with the second end 364 of device 330. The shaft 508a includes a monopolar connection 550a that can be exposed on the surface of the shaft 508a proximate the first end 564a.

FIG. 15 illustrates device 530a configured in bipolar mode with shaft 508a extended as indicated, for example by device 330 in FIG. 8. When the shaft 508a is extended as described, return bipolar connection 572a is electrically coupled to return connection 568. Further, active bipolar connection 570a is electrically coupled to cut connection 562, coagulation connection 564, and active connection 566. The monopolar electrode blade 532a is not electrically coupled to the switch mechanism 582a.

When device 530a is configured in the bipolar mode and the shaft 508a is extended as described, closing either the cut switch 512 or the coagulation switch 514 will provide an electrical signal directly between the switch input 594 and the active input 596, i.e., the connection will electrically short or include a resistance of about 0 ohms, to indicate to the electrosurgical unit 10 that the device 530a is to be operated in a bipolar mode. Accordingly, the third RF energy level corresponding with a bipolar mode is provided to the active input and thus to the active electrode end 522a and returned through the tissue via the return electrode end 522b.

FIG. 16 illustrates device 530a configured in monopolar mode with shaft 508a retracted as indicated, for example by device 330 in FIG. 7. When the shaft 508a is retracted as described, the active bipolar connection 570a and return bipolar connection 572a are decoupled from the switch mechanism 582a. Instead, the active connection 566 and the monopolar active connection 560 of the interface 586a are electrically coupled together via the monopolar connection 550a in the shaft 508a such that the monopolar electrode blade 532a is electrically coupled to the switch mechanism 582a.

When device 530a is configured in the monopolar mode and the shaft 508a is retracted as described, closing the cut switch 512 provides an electrical signal between the switch input 594 and the active input 596 through the cut resistor 536 to indicate to the electrosurgical unit 10 that the device 530a is to be operated in a cut function of the monopolar mode. Accordingly, the first RF energy level corresponding with a cut function is provided to the active input 596 and thus to the monopolar electrode blade 532a and returned through the tissue via a ground dispersive electrode (not shown).

When device 530a is configured in the monopolar mode and the shaft 508a is retracted as described, closing the coagulation switch 514 provides an electrical signal between the switch input 594 and the active input 596 through the coagulation resistor 538 to indicate to the electrosurgical unit 10 that the device 530a is to be operated in a coagulation function of the monopolar mode. Accordingly, the second RF energy level corresponding with a coagulation function is provided to the active input 596 and thus to the monopolar electrode blade 532a and returned through the tissue via a ground dispersive electrode (not shown).

Figure 17:
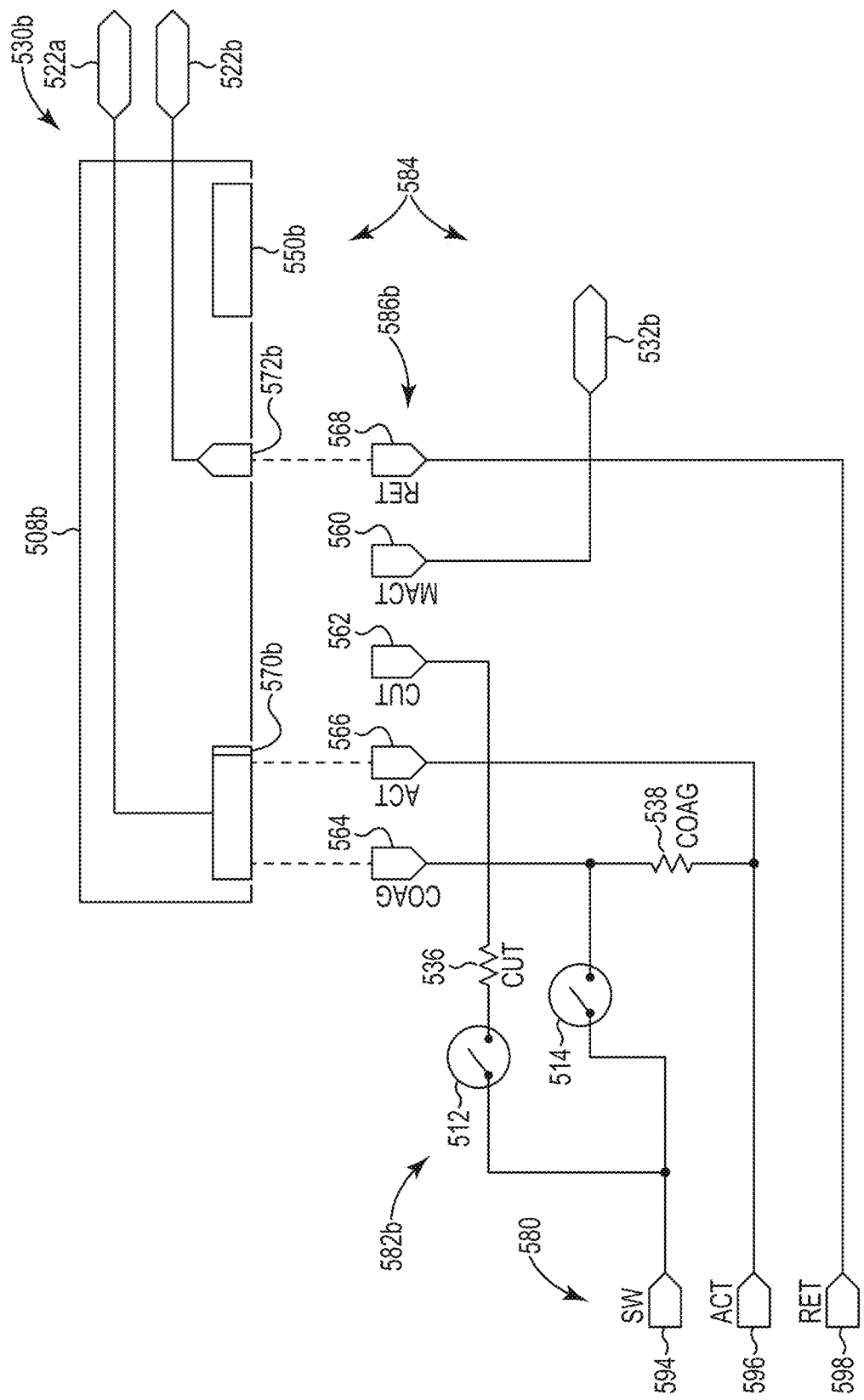
FIG. 17 is a schematic view of a circuit diagram of a handheld electrosurgical device of FIG. 4 configured as a second example the electrosurgical device of FIG. 8 in a bipolar mode.
Figure 18:
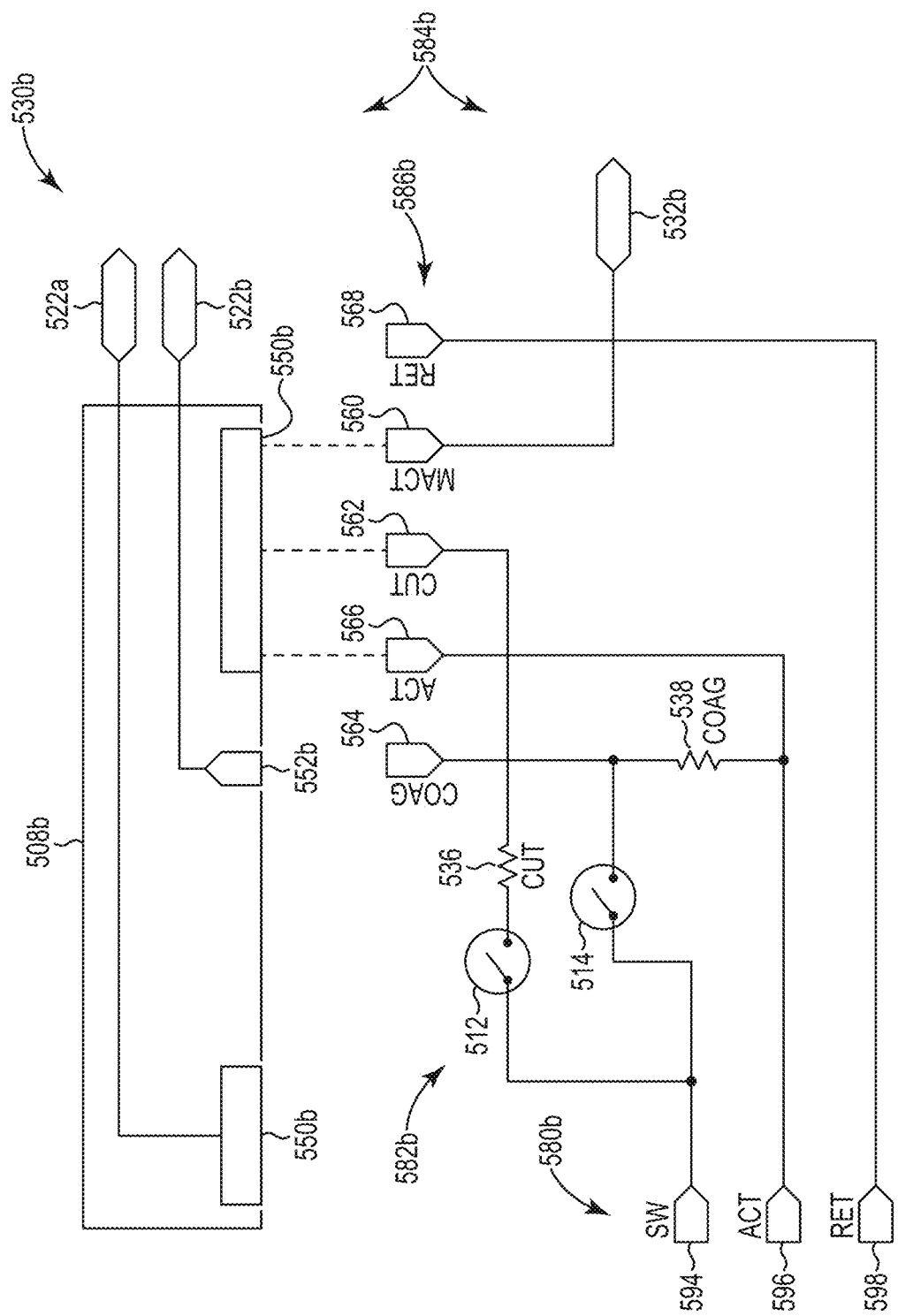
FIG. 18 is a schematic view of a circuit diagram of a handheld electrosurgical device of FIG. 4 configured as a second example the electrosurgical device of FIG. 7 in a monopolar mode.

FIGS. 17-18 illustrate example device 530b having inputs 580b, switch mechanism 582b, interface 586b, and electrode tips 584b configured to work with switch mechanism 582b. Switch mechanism 582b includes a cut switch 512 and cut resistor 536 coupled in series between the switch input 594 and cut switch connection 562. Switch mechanism 582b also includes a coagulation switch 514 and coagulation resistor 538 coupled in series between the switch input 594 and the active input 596. In the example illustrated, the coagulation switch connection 564 is electrically coupled between the coagulation switch 514 and the coagulation resistor 538. Also, the active input 596 is directly coupled to the active connection 566, and the return input 598 is directly coupled to the return connection 568.

Example device 530b further includes a monopolar electrode tip 510b configured to operate the device 530b in a monopolar mode. The monopolar electrode tip 510b includes a monopolar electrode blade 532b that is electrically coupled to monopolar active connection 560b.

Example device 530b further includes a bipolar shaft 508b that includes an active electrode end 522a and a return electrode end 522b extending from the shaft 508b at, for example, a first end 562b that may correspond with first end 362 of device 330. The active electrode end 522a is electrically coupled via conductor to an active bipolar connection 570b, and the return electrode end 522b is electrically coupled via conductor to a return bipolar connection 572b. In the example, connections 570b, 572b are exposed on the surface of the shaft 508b proximate the second end 564b that may correspond with the second end 364 of device 330. The shaft 508b includes a monopolar connection 550b that can be exposed on the surface of the shaft 508b proximate the first end 564b.

FIG. 17 illustrates device 530b configured in bipolar mode with shaft 508b extended as indicated, for example by device 330 in FIG. 8. When the shaft 508b is extended as described, return bipolar connection 572b is electrically coupled to return connection 568. Further, active bipolar connection 570b is electrically coupled to coagulation connection 564 and active connection 566. The monopolar electrode blade 532b is not electrically coupled to the switch mechanism 582b.

When device 530b is configured in the bipolar mode and the shaft 508a is extended as described, closing the coagulation switch 514 will provide an electrical signal directly between the switch input 594 and the active input 596, i.e., the connection will electrically short or include a resistance of about 0 ohms, to indicate to the electrosurgical unit 10 that the device 530b is to be operated in a bipolar mode. Accordingly, the third RF energy level corresponding with a bipolar mode is provided to the active input and thus to the active electrode end 522a and returned through the tissue via the return electrode end 522b. In the example of bipolar electrode tip 508b, closing the cut switch 512 will not active the device 530b.

FIG. 18 illustrates device 530b configured in monopolar mode with shaft 508b retracted as indicated, for example by device 330 in FIG. 7. When the shaft 508b is retracted as described, the active bipolar connection 570b and return bipolar connection 572b are decoupled from the switch mechanism 582b. Instead, the cut connection 562, active connection 566 and the monopolar active connection 560 of the interface 586b are electrically coupled together via the monopolar connection 550b in the shaft 508b such that the monopolar electrode blade 532b is electrically coupled to the switch mechanism 582b.

When device 530b is configured in the monopolar mode and the shaft 508b is retracted as described, closing the cut switch 512 provides an electrical signal between the switch input 594 and the active input 596 through the cut resistor 536 to indicate to the electrosurgical unit 10 that the device 530b is to be operated in a cut function of the monopolar mode. Accordingly, the first RF energy level corresponding with a cut function is provided to the active input 596 and thus to the monopolar electrode blade 532b and returned through the tissue via a ground dispersive electrode (not shown).

When device 530b is configured in the monopolar mode and the shaft 508b is retracted as described, closing the coagulation switch 514 provides an electrical signal between the switch input 594 and the active input 596 through the coagulation resistor 538 to indicate to the electrosurgical unit 10 that the device 530b is to be operated in a coagulation function of the monopolar mode. Accordingly, the second RF energy level corresponding with a coagulation function is provided to the active input 596 and thus to the monopolar electrode blade 532b and returned through the tissue via a ground dispersive electrode (not shown).

In one example, the connections of the interface 586a, 586b can be constructed from pogo pins and the electrical connections 570a, 572a, 550a, and 570b, 572, 550b on shafts 508a, 508b, respectively, can be constructed from conductive pads to provide for a robust electrical connections that can also be used to releasably hold the shafts 508a, 508b in place with respect to the interfaces 586a, 586b. Connections on the interfaces 586a, 586b can also be constructed from conductive bumps that can mate with conductive flat pads or detents on the shaft 508a, 508b. Pogo pins may be included on the shafts 508a, 508b and the interface may be included on the interfaces 586a, 586b. Still other configurations are possible.

Further, one skilled in the art can now readily recognize electrical connections of a device having a monopolar blade disposed on the extendable/retractable shaft and bipolar electrode electrodes fixed with respect to movement of the switch mechanism and/or interface. Further, one skilled in the art can now readily recognized electrical connections of a device having both the monopolar blade and the bipolar electrode ends movable with respect to the switch mechanism and/or interface.

Although the present disclosure has been described with reference to preferred embodiments, workers skilled in the art will recognize that changes can be made in form and detail without departing from the spirit and scope of the present disclosure.

What is claimed is:

1. A multipurpose electrosurgical device, comprising:
   a handpiece having a conductive input and a conductive output, wherein the conductive input is a three-conductor input of a switch input conductor, an active input conductor, and a return input conductor, and the conductive output including a first function output conductor, a second function output conductor, an active output conductor operably coupled to the active input conductor, and a return output conductor operably coupled to the return input conductor;
   a plurality of electrode tips coupleable to the handpiece, the plurality of electrode tips including a first electrode tip to selectively configure the device in a monopolar mode, the first electrode tip operably coupleable to at least the active output conductor of the active output conductor, the first function output conductor and the second function output conductor, and a second electrode tip to selectively configure the device in a bipolar mode, the second electrode tip having a first output electrode operably couplable to at least two of the active output conductor of the active output conductor, the first function output conductor and the second function output conductor and a second output electrode operably coupleable to the return output conductor; and
   a switching mechanism included in the handpiece and coupled to the input, the switching mechanism having a plurality of user-selectable configuration to provide signals from the input to the plurality of electrode tips including a first switch configuration wherein the first electrode tip corresponds with a first function in the monopolar mode and a second switch configuration wherein the first electrode tip corresponds with a second function in the monopolar mode and to provide a signal from the input to the second electrode tip corresponding with a third function in the bipolar mode.

2. The multipurpose electrosurgical device of claim 1 wherein the switching mechanism includes two switches to provide the first, second, and third functions.

3. The multipurpose electrosurgical device of claim 1 wherein the first function is a cut function, the second function is a coagulation function, and the third function is a hemostatic sealing function.

4. The multipurpose electrosurgical device of claim 1 wherein the switch input conductor configured to detect the function selected by the switching mechanism, and the active input configured to receive a source of RF energy corresponding to the selected to function.

5. The multipurpose electrosurgical device of claim 1 wherein the first electrode tip includes a monopolar electrode and the second electrode tip includes bipolar electrodes.

6. The multipurpose electrosurgical device of claim 1 wherein the plurality of electrode tips are removably coupleable to the switching mechanism.

7. The multipurpose electrosurgical device of claim 6 wherein the plurality of electrode tips are removably coupleable to the handpiece.

8. A multipurpose electrosurgical device comprising:
a handpiece having a switch input conductor and an active input conductor operably coupled to a first function output conductor, a second function output conductor and an active output conductor in the handpiece, the handpiece having a return input conductor operably coupled to a return output conductor in the handpiece;
a switching mechanism included in the handpiece operably coupled to the switch input conductor to select a first function and a second function in a first mode and to select a third function in a second mode;
a first electrode tip fixedly coupled to the handpiece and selectively couplable to the handpiece; and
a second electrode tip transitionable between a retracted position and a protracted position with respect to the handpiece and selectively electrically couplable to at least two of the first function output conductor, the second function output conductor, and the active output conductor, wherein the second electrode tip is selectively coupled to the switching mechanism in the protracted position in one of the first mode and the second mode, and the first electrode tip is selectively coupled to the switching mechanism in the other of the first mode and the second mode when the second electrode tip is in the retracted position, and wherein one of the first electrode tip and the second electrode tip is selectively decoupled from the switching mechanism when the other of the first electrode tip and the second electrode tip is selectively coupled to the switching mechanism.

9. The multipurpose electrosurgical device of claim 8 wherein the first electrode tip includes a monopolar electrode and the second electrode tip includes bipolar electrodes.

10. The multipurpose electrosurgical device of claim 8 including an axially retractable and protractible shaft including the second electrode tip.

11. The multipurpose electrosurgical device of claim 10 wherein the first electrode tip is distal to the second electrode tip in the retracted position and the second electrode tip is distal to the first electrode tip in the protracted position.

12. The multipurpose electrosurgical device of claim 8 wherein the switch mechanism includes:
the switch input conductor configured to be coupled to an energy detection system in an electrosurgical device; and
the active input conductor configured to be coupled to a source of RF energy; and
wherein the active input conductor is operably configured to be coupled to the first and second electrode tips via the switch mechanism.

13. A multipurpose electrosurgical device configured to be coupled to an electrosurgical unit for providing a source of RF energy in a plurality of RF energy levels, the multipurpose electrosurgical device including:
a handpiece having an input and an output, the output configured to receive one electrode tip, the input receiving no more than three conductors including a return conductor for use in a bipolar mode;
a plurality of electrode tips coupleable to the output of the handpiece, the plurality of electrode tips including:
a first electrode tip having a monopolar active electrode to selectively configure the device in a monopolar mode; and
a second electrode tip having a bipolar active electrode to selectively configure the device in the bipolar mode; and
the handpiece including a switch mechanism operably coupleable to the monopolar active electrode and the bipolar active electrode, the switch mechanism comprising:
a first conductor configured to be coupled to an energy detection system in the electrosurgical unit; and
a second conductor configured to be coupled to the source of RF energy;
wherein the second conductor is operably configured to be coupled to the monopolar and bipolar active electrodes, via the switch mechanism;
wherein the monopolar active electrode is activated at a first monopolar RF energy level when the switch mechanism electrically couples the first conductor to the second conductor via a first circuit element in the monopolar mode;
wherein the monopolar active electrode is activated at a second monopolar RF energy level when the switch mechanism electrically couples the first conductor to the second conductor via a second circuit element in the monopolar mode; and
wherein the bipolar active electrode is activated at a bipolar RF energy level when the switch mechanism electrically couples the first conductor directly to the second conductor in the bipolar mode.

14. The multipurpose electrosurgical device of claim 13 wherein the circuit elements are resistors.

15. A method of selectively configuring an electrosurgical device for use in a bipolar mode and a monopolar mode, the method including,
receiving at a handpiece a switch input conductor, an active input conductor, and a return input conductor via no more than a three-conductor input;
providing in the handpiece a first function output conductor and a second output conductor operably coupled to the switch input conductor, an active output conductor operably coupled to the active input conductor, and a return output conductor operably coupled to the return input conductor;
configuring the device in a monopolar mode with a monopolar electrode blade coupled to the handpiece;
activating the monopolar electrode blade with a first RF energy in the monopolar mode by closing a first switch, and activating a second RF energy in the monopolar by closing a second switch, the first and second switches coupled to the active output conductor;
configuring the device in a bipolar mode with a pair of bipolar electrodes coupled to the handpiece; and
activating a bipolar electrode of the pair of bipolar electrodes with a third RF energy by closing one of the first and second switches in the bipolar mode.

16. The method of claim 15 wherein configuring the device in a bipolar mode includes disposing the pair of bipolar electrodes distal most on the device.

17. The method of claim 16 wherein the disposing includes attaching or extending the pair of bipolar electrodes distally from the electrosurgical device.

18. The method of claim 15 wherein configuring the device in a monopolar mode includes disposing the electrode blade distal most on the device.

19. The method of claim 18 wherein the disposing the monopolar electrode blade includes attaching the monopolar blade to a handpiece.

20. The method of claim 18 wherein the disposing includes retracting the pair of bipolar electrodes into a handpiece.

* * * * *